(12) United States Patent
Nishio et al.

(10) Patent No.: US 11,259,836 B2
(45) Date of Patent: Mar. 1, 2022

(54) MEDICAL DEVICE AND TREATMENT METHOD

(71) Applicant: TERUMO KABUSHIKI KAISHA, Tokyo (JP)

(72) Inventors: Kousuke Nishio, Machida (JP); Tomonori Hatta, San Jose, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 188 days.

(21) Appl. No.: 16/583,368

(22) Filed: Sep. 26, 2019

(65) Prior Publication Data
US 2020/0015844 A1 Jan. 16, 2020

Related U.S. Application Data

(63) Continuation of application No. PCT/JP2018/012851, filed on Mar. 28, 2018.

(30) Foreign Application Priority Data

Mar. 28, 2017 (JP) .............................. JP2017-062165

(51) Int. Cl.
*A61B 17/3207* (2006.01)
(52) U.S. Cl.
CPC ............................ *A61B 17/320783* (2013.01)
(58) Field of Classification Search
CPC .... A61B 17/320758; A61B 17/320783; A61B 17/320725
See application file for complete search history.

(56) References Cited

U.S. PATENT DOCUMENTS

| | | | |
|---|---|---|---|
| 6,183,487 B1 * | 2/2001 | Barry | A61B 17/320758 606/159 |
| 7,252,674 B2 | 8/2007 | Wyzgala et al. | |
| 2002/0151917 A1 * | 10/2002 | Barry | A61B 17/320758 606/159 |
| 2009/0099581 A1 | 4/2009 | Kim et al. | |
| 2014/0005699 A1 * | 1/2014 | Bonnette | A61B 17/320725 606/159 |

FOREIGN PATENT DOCUMENTS

| | | |
|---|---|---|
| JP | H09509605 A | 9/1997 |
| JP | 2003504090 A | 2/2003 |

OTHER PUBLICATIONS

International Search Report (PCT/ISA/210) and translation and Written Opinion (PCT/ISA/237) dated Jun. 5, 2018, by the Japanese Patent Office as the International Searching Authority for International Application No. PCT/JP2018/012851.

* cited by examiner

*Primary Examiner* — Tuan V Nguyen
(74) *Attorney, Agent, or Firm* — Buchanan Ingersoll & Rooney PC

(57) ABSTRACT

A medical device and a treatment method are disclosed, which can effectively cut an object inside a biological lumen and can improve safety by reducing damage to a biological tissue. A medical device is disclosed for cutting the object inside the biological lumen. A structure rotated by a drive shaft has a first cutting portion, a second cutting portion located more proximal than the first cutting portion, a first non-cutting portion located between the first cutting portion and the second cutting portion, and a second non-cutting portion located on a proximal side of the second cutting portion.

20 Claims, 8 Drawing Sheets

MEDICAL DEVICE AND TREATMENT METHOD

CROSS-REFERENCES TO RELATED APPLICATIONS

This application is a continuation of International Application No. PCT/JP2018/012851 filed on Mar. 28, 2018, which claims priority to Japanese Application No. 2017-062165 filed on Mar. 28, 2017, the entire content of both of which is incorporated herein by reference.

FIELD OF THE DISCLOSURE

The present disclosure relates to a medical device and a treatment method for cutting an object from an inner wall surface of a biological lumen.

BACKGROUND DISCUSSION

Methods for treatment of a stenosed site caused by a plaque or a thrombus of a coronary artery can include a percutaneous transluminal coronary angioplasty (PTCA) using a balloon to widen a blood vessel and a method of causing a reticulated or coil-shaped stent to indwell on the inside of the blood vessel as a support for the blood vessel. However, these methods are less likely to be applicable to a case where the plaque of the stenosed site is calcified and hardened, or a case where the stenosed site appears in a bifurcated portion of the coronary artery. Methods of treatments which can be used in this case can include an atherectomy for cutting a stenosis such as the plaque and the thrombus.

As a device for the atherectomy, for example, U.S. Pat. No. 7,252,674 discloses a device having diamond particles (polishing materials) attached to an outer surface of a rotating body located in a distal portion of a catheter. The rotating body is rotated inside the coronary artery, thereby cutting the stenosis.

In the device disclosed in U.S. Pat. No. 7,252,674, the polishing material attached to the rotating body may come into contact with a vascular wall. For example, in a case where the stenosis is biased to a portion in a circumferential direction of the vascular wall, the rotating body can come into contact with the vascular wall on an opposite side on which there may or may not have any stenosis. Therefore, a risk of causing damage to a normal blood vessel can increase.

SUMMARY

A medical device and a treatment method are disclosed, which can effectively cut an object inside a biological lumen and can improve safety by reducing damage to a biological tissue.

According to an aspect of the present disclosure, a medical device for cutting an object inside a biological lumen, which includes a rotatable drive shaft, and a structure configured to be connected with a distal portion of the drive shaft and rotatable by the drive shaft. The structure has a cutting portion having an outer peripheral surface capable of cutting the object, and a non-cutting portion having an outer peripheral surface smoother than the cutting portion with respect to a biological tissue. The cutting portion has a first cutting portion and a second cutting portion located more proximal than the first cutting portion. The non-cutting portion has a first non-cutting portion located between the first cutting portion and the second cutting portion. The structure or a tubular body disposed on a proximal side of the second cutting portion of the structure has a second non-cutting portion located on the proximal side of the second cutting portion. Equations (A) to (E) below are all satisfied, wherein a represents the maximum radius of the outer peripheral surface of the first cutting portion, b represents the maximum radius of the outer peripheral surface of the second cutting portion, c represents the maximum radius of the outer peripheral surface of the first non-cutting portion, d represents the maximum radius of the outer peripheral surface of the second non-cutting portion, L1 represents the axial length of the first non-cutting portion, and L2 represents the axial length of the second cutting portion.

$$a < b \quad \text{Equation (A)}$$

$$c < d \quad \text{Equation (B)}$$

$$d \leq b \quad \text{Equation (C)}$$

$$a < d \quad \text{Equation (D)}$$

$$L1 < L2 \quad \text{Equation (E)}$$

In addition, according to another aspect of the present disclosure, a medical device for cutting an object inside a biological lumen, which includes a rotatable drive shaft, and a structure configured to be connected with a distal portion of the drive shaft and rotatable by the drive shaft. The structure has a cutting portion having an outer peripheral surface capable of cutting the object, and a non-cutting portion having an outer peripheral surface smoother than the cutting portion. The non-cutting portion has a first non-cutting portion located on a distal side of the cutting portion. The structure or a tubular body disposed on a proximal side of the cutting portion of the structure has a second non-cutting portion located on a proximal portion of the cutting portion. Equations (B) and (H) below are satisfied, wherein c represents the maximum radius of the outer peripheral surface of the first non-cutting portion, d represents the maximum radius of the outer peripheral surface of the second non-cutting portion, and e represents a deviation distance from a tangent to the first non-cutting portion and the second non-cutting portion to a most distant portion of the cutting portion, which is most distant in a direction perpendicular to the tangent and away from the central axis of the structure, in a cross section along the axial direction of the structure.

$$c < d \quad \text{Equation (B)}$$

$$e < 150 \, \mu m \quad \text{Equation (H)}$$

In addition, according to still another aspect of the present disclosure, a medical device is disclosed for cutting an object inside a biological lumen, which includes a rotatable drive shaft, and a structure configured to be connected with a distal portion of the drive shaft and rotatable by the drive shaft. The structure has a cutting portion having an outer peripheral surface capable of cutting the object, and a non-cutting portion having an outer peripheral surface smoother than the cutting portion. The cutting portion has a first cutting portion and a second cutting portion located more proximal than the first cutting portion. The non-cutting portion has a first non-cutting portion located between the first cutting portion and the second cutting portion. The structure or a tubular body disposed on the proximal side of the second cutting portion of the structure has a second non-cutting portion located on the proximal portion of the second cutting portion. The second cutting portion gradually increases in diameter from a distal side to a proximal side, and a maximum outer diameter of the second cutting portion is located on the proximal portion of the second cutting portion. At least a portion of the second cutting portion is located outside the tangent to the first non-cutting portion and the second non-cutting portion in a cross section along the axial direction of the structure.

According to still another aspect of the present disclosure a treatment method is disclosed for cutting an object inside a biological lumen by using the above-described medical device. The treatment method includes a step of inserting the structure into the biological lumen, a step of bringing the first non-cutting portion into smooth contact with a biological tissue by moving the structure to the distal side while rotating the structure, and causing the first cutting portion to cut the object, a step of bringing the first non-cutting portion and the second non-cutting portion into contact with the biological tissue by moving the structure to the distal side, and rotating the structure so as to cause the second cutting portion to cut the object, and a step of removing the structure from the inside of the biological lumen.

In accordance with an aspect, the medical device configured as described above has the first cutting portion and the second cutting portion which interpose the first non-cutting portion between the first cutting portion and the second cutting portion. Accordingly, the medical device cuts the object in a stepwise manner. In this manner, while safety can be relatively ensured, the object can be deeply (largely) cut at a final stage. In the medical device, the first cutting portion having the maximum radius a, which is smaller than the maximum radius b of the second cutting portion and the maximum radius d of the second non-cutting portion is disposed more distal than the first non-cutting portion. Accordingly, before the object is deeply cut by the second cutting portion, the object can be cut by the first cutting portion while the first non-cutting portion prevents damage to the biological tissue. In addition, in the medical device, compared to the first cutting portion, the object inside the biological lumen can be deeply cut by the second cutting portion including the maximum radius b which is larger than the maximum radius a of the first cutting portion and is equal to or larger than the maximum radius d of the second non-cutting portion. Then, the second cutting portion is interposed between the first non-cutting portion and the second non-cutting portion. Accordingly, the biological tissue can be relatively prevented from being excessively damaged by the second cutting portion. In addition, with the medical devices disclosed, improved cutting capacity and improved safety can be compatibly achieved. Furthermore, the axial length L1 of the first non-cutting portion is smaller than the axial length L2 of the second cutting portion. Accordingly, when the object is cut by the second cutting portion, a position where the rotating first non-cutting portion comes into contact with the biological tissue can be stabilized. Therefore, the rotating structure is stably supported by the first non-cutting portion, and the improved cutting capacity and safety can be maintained. Therefore, the medical device can rather effectively cut the object inside the biological lumen and the safety can be improved by reducing the damage to the biological tissue.

The medical device according to another aspect configured as described above satisfies Equation (B). In this manner, the second non-cutting portion becomes larger than the first non-cutting portion. Therefore, the medical device can relatively freely pass through the blood vessel. Furthermore, the medical device satisfies Equation (H). In this manner, the deviation distance e becomes smaller than a thickness of a vascular wall. Accordingly, the safety of the medical device can be improved.

The medical device according to still another aspect configured as described above can cause the second cutting portion to rather effectively cut the object inside the biological lumen. The damage to the biological tissue can be reduced by the second non-cutting portion, and thus, the relatively safety can be improved.

According to the treatment method configured as described above, the first non-cutting portion is brought into relatively smooth contact with the biological tissue, and the object is cut by the first cutting portion. Accordingly, before the object is deeply cut by the second cutting portion, the object can be cut by the first cutting portion while the first non-cutting portion prevents the damage to the biological tissue. Then, the structure is moved to the distal side. Thereafter, while the damage to the biological tissue can be prevented by the first non-cutting portion and the second non-cutting portion, and wherein the second cutting portion is interposed between the first non-cutting portion and the second non-cutting portion, the object can be effectively cut by the second cutting portion having the larger outer diameter than the first cutting portion. Therefore, according to the treatment method, the object inside the biological lumen can be effectively cut, and the relative safety can be improved by reducing the damage to the biological tissue.

BRIEF DESCRIPTION OF THE DRAWINGS

FIGS. 4A-4D are schematic sectional views illustrating an intravascular state when a medical procedure is performed, and wherein FIG. 4A illustrates a state when the medical device is inserted into a blood vessel along a guide wire, FIG. 4B illustrates a state where a stenosed site is cut by a first cutting portion, FIG. 4C illustrates a state where the stenosed site is cut by a second cutting portion, and FIG. 4D illustrates a state where the stenosed site is cut by an oscillating structure.

DETAILED DESCRIPTION

Figure 1:
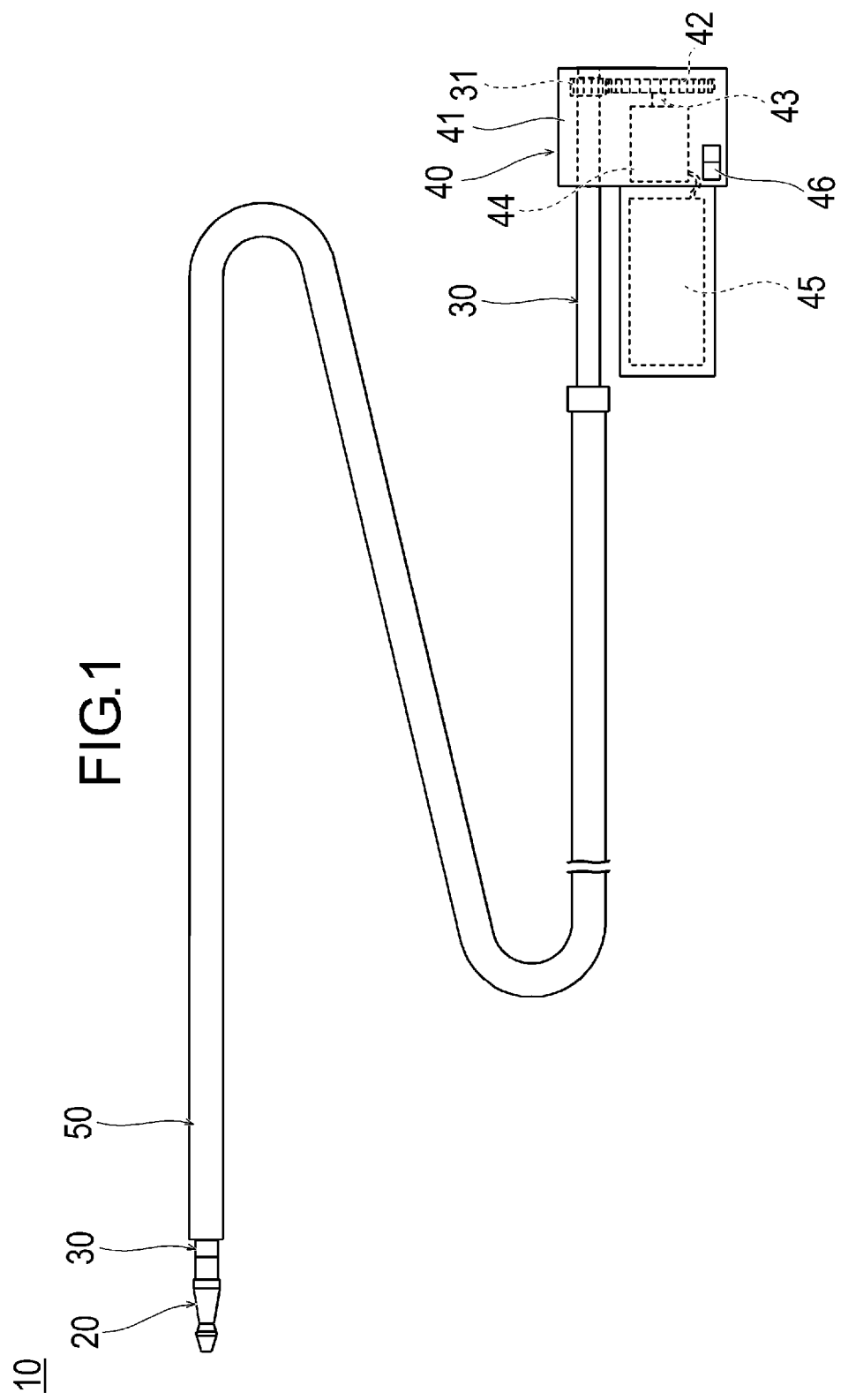
FIG. 1 is a plan view illustrating a medical device according to an embodiment.

Hereinafter, an embodiment according to the present disclosure will be described with reference to the drawings. Dimensional proportions in the drawings are exaggerated and different from actual proportions for convenience of description, in some cases.

A medical device 10 according to the embodiment of the present disclosure can be used for medical treatment (treatment) for cutting a stenosed site or an occluded site caused by a plaque or a thrombus inside a blood vessel. In the description herein, a side on which the device is inserted into the blood vessel will be referred to as a "distal side", and an operator's hand side will be referred to as a "proximal side".

Figure 2:
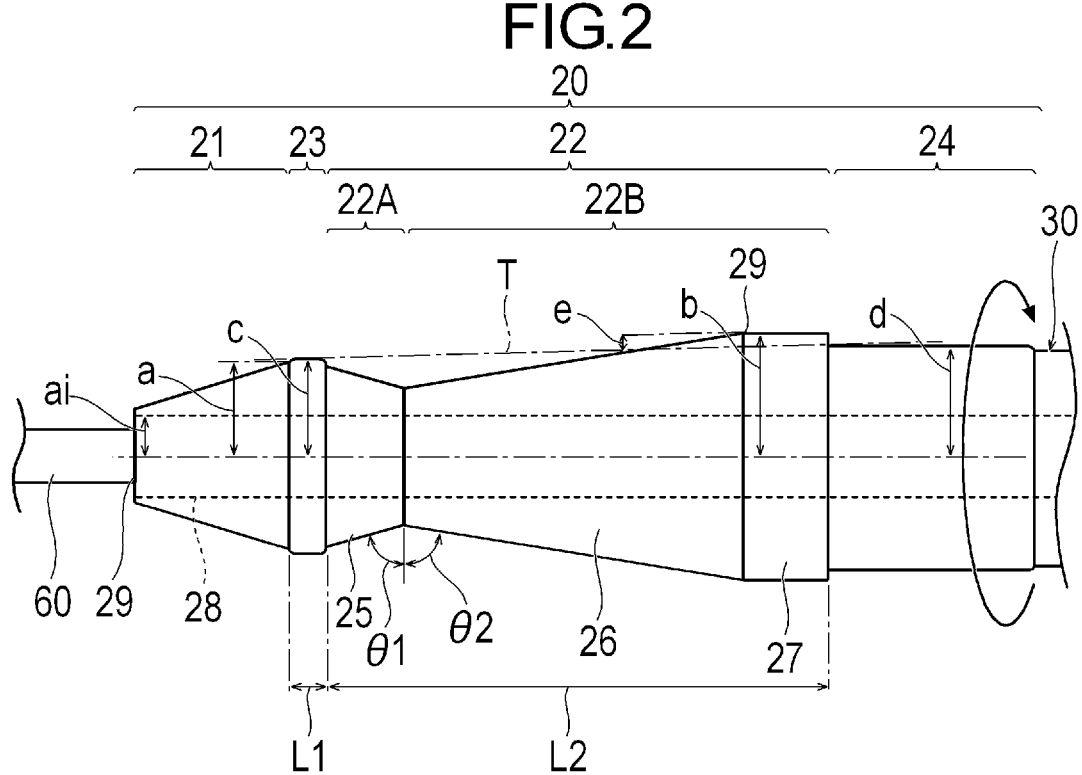
FIG. 2 is a plan view illustrating a distal portion of the medical device according to the embodiment.

As illustrated in FIGS. 1 and 2, the medical device 10 can include a rotatable structure 20, a drive shaft 30 for rotating the structure 20, an operation unit 40 disposed on the operator's hand side, and an outer sheath 50 which can accommodate the structure 20.

The structure 20 includes a cutting portion having an outer peripheral surface for cutting a stenosed site S (refer to FIG. 4A) serving as an object inside a biological lumen, and a non-cutting portion having an outer peripheral surface which rather smoothly comes into contact a biological tissue than the cutting portion and which does not relatively damage the biological tissue. In accordance with an exemplary embodiment, the cutting portion includes a first cutting portion 21 located on a most distal side of the structure 20 and a second cutting portion 22 located more proximal than the first cutting portion 21. The non-cutting portion includes a first non-cutting portion 23 located between the first cutting portion 21 and the second cutting portion 22, and a second non-cutting portion 24 located more proximal than the second cutting portion 22. In accordance with an exemplary embodiment, for example, the structure 20 has the first cutting portion 21, the first non-cutting portion 23, the second cutting portion 22, and the second non-cutting portion 24 which are arranged side by side from a distal end to the proximal side. In accordance with an exemplary embodiment, it can be, for example, preferable that a range of the structure 20 including at least the first cutting portion 21, the first non-cutting portion 23, the second cutting portion 22, and the second non-cutting portion 24 is a rigid body which is hardly bent (for example, during rotation of the structure). In this manner, a positional relationship among the first cutting portion 21, the first non-cutting portion 23, the second cutting portion 22, and the second non-cutting portion 24 can be changed relatively little during a process of cutting the stenosed site S. In accordance with an exemplary embodiment, distal portions of the first cutting portion 21, the first non-cutting portion 23, the second cutting portion 22, the second non-cutting portion 24, and a distal portion of the drive shaft 30 have a common axis.

In accordance with an exemplary embodiment, the first cutting portion 21 is located in a most distal portion of the structure 20. The first cutting portion 21 has an outer peripheral surface whose outer diameter decreases in a tapered shape toward the distal side. The outer peripheral surface of the first cutting portion 21 has a circular shape in an axially orthogonal cross section. In accordance with an exemplary embodiment, a maximum radius a of the outer peripheral surface of the first cutting portion 21 is a radius of the outer peripheral surface of a most proximal portion of the first cutting portion 21. The maximum radius a of the first cutting portion 21 is the maximum radius of the range in which the first cutting portion 21 can perform cutting. The structure 20 can internally have a guide wire lumen 28 which communicates with a lumen of the drive shaft 30 and into which a guide wire 60 can be inserted. Therefore, the first cutting portion 21 has a minimum radius ai in the range where cutting can be performed. The minimum radius ai in the range where the first cutting portion 21 can perform cutting is substantially equal to the radius of an inner peripheral surface of the guide wire lumen 28. In accordance with an aspect, an axis of the guide wire lumen 28 coincides with an axis of the outer peripheral surface of the structure 20. The guide wire lumen 28 has a distal side opening portion 20A which is open in the structure 20.

In accordance with an exemplary embodiment, the second cutting portion 22 includes a distal cutting portion 22A located on the distal side and a proximal cutting portion 22B located on the proximal side. The distal cutting portion 22A has a diameter increasing portion 25 located in the distal portion of the second cutting portion 22. The proximal cutting portion 22B includes a diameter decreasing portion 26 located on the proximal side of the diameter increasing portion 25, and a uniform diameter portion 27 located on the proximal side of the diameter decreasing portion 26. The uniform diameter portion 27 has an outer peripheral surface whose outer diameter is uniform toward the distal side from the second non-cutting portion 24. In accordance with an exemplary embodiment, the outer peripheral surface of the uniform diameter portion 27 has a circular shape in the axially orthogonal cross section. The diameter decreasing portion 26 has an outer peripheral surface whose outer diameter decreases in a tapered shape from the uniform diameter portion 27 toward the distal side. The outer peripheral surface of the diameter decreasing portion 26 has a circular shape in the axially orthogonal cross section. The diameter increasing portion 25 has an outer peripheral surface whose outer diameter increases in a tapered shape toward the distal side from the diameter decreasing portion 26 to the first non-cutting portion 23. The outer peripheral surface of the diameter increasing portion 25 has a circular shape in the axially orthogonal cross section.

The diameter increasing portion 25 and the diameter decreasing portion 26 are interlocked (i.e., connected) with each other so that the outer peripheral surface has a V-shape in a longitudinal cross section passing through the axis. An angle $\theta 1$ of the diameter increasing portion 25 with respect to the axially orthogonal cross section is equal to or smaller than an angle $\theta 2$ of the diameter decreasing portion 26 with respect to the axially orthogonal cross section. Furthermore, the maximum radius of the outer peripheral surface of the diameter decreasing portion 26 is larger than the maximum radius of the outer peripheral surface of the diameter increasing portion 25. Therefore, the diameter decreasing portion 26 can be disposed in a wider range in the axial direction than the diameter increasing portion 25. In accordance with an exemplary embodiment, the diameter decreasing portion 26 cuts the stenosed site S, mainly when the medical device 10 is pushed (i.e., moved in distal direction into the blood vessel. The diameter increasing portion 25 cuts the stenosed site S, mainly when the medical device 10 is pulled out (i.e., moved in a proximal direction) of the blood vessel. Normally, more objects need to be cut when the medical device 10 is pushed into the blood vessel, compared to when the medical device 10 is pulled out of the blood vessel. Therefore, a shape suitable for cutting can be obtained by setting the angle $\theta 1$ to be equal to or smaller than the angle $\theta 2$.

In accordance with an exemplary embodiment, the uniform diameter portion 27 is a portion having a maximum radius b of the second cutting portion 22. The maximum radius b of the second cutting portion 22 coincides with the radius of the outer peripheral surface of the proximal end portion of the diameter decreasing portion 26. The uniform diameter portion 27 can efficiently cut the stenosed site S in a wide range since the uniform diameter portion 27 has a predetermined length in the axial direction.

Figure 3:
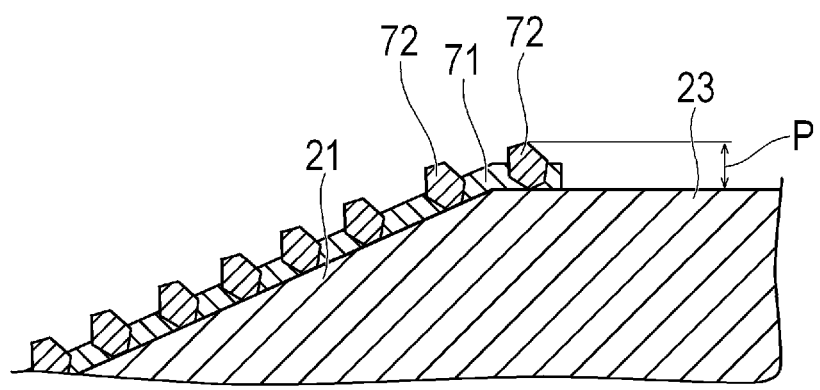
FIG. 3 is an enlarged sectional view illustrating the vicinity of a surface of a structure.

As illustrated in FIG. 3, abrasive grains 72, for example, polishing materials such as diamond particles are fixed to the respective outer surfaces of the first cutting portion 21 and the second cutting portion 22 by a fixing layer 71 such as a nickel plating layer. Therefore, the fixing layer 71 and the abrasive grains 72 can be located beyond the outer diameter of the first non-cutting portion 23 in a portion adjacent to the first non-cutting portion 23 in the first cutting portion 21 and the second cutting portion 22. Similarly, the fixing layer 71 and the abrasive grains 72 can be located beyond the outer diameter of the second non-cutting portion 24 in a portion adjacent to the second non-cutting portion 24 in the second cutting portion 22. However, an axial length and an area of a range having the abrasive grains 72 and the fixing layer 71 which has the larger outer diameter than the first non-cutting portion 23 (or the second non-cutting portion 24) are extremely smaller than the axial length and the area of the outer peripheral surface of the first non-cutting portion 23 (or the second non-cutting portion 24). Therefore, the abrasive grains 72 located beyond (i.e., outside of) the outer diameter of the first non-cutting portion 23 (or the second non-cutting portion 24) contribute to the polishing in a relatively limited manner. A maximum protruding amount P which is a maximum value of the amount where the abrasive grains 72 and the fixing layer 71 protrude outward in a radial direction can be 100 µm, for example. Preferably, the maximum protruding amount P, for example, is 50 µm, more preferably 30 µm, and still more preferably 20 µm. Therefore, in a configuration in which the abrasive grains 72 or the fixing layer 71 further protrudes in a minute range than the first non-cutting portion 23, a maximum radius c of the first non-cutting portion 23 is substantially equal to or larger than the maximum radius a of the first cutting portion 21.

As illustrated in FIG. 2, the first non-cutting portion 23 is located between the first cutting portion 21 and the second cutting portion 22. In accordance with an exemplary embodiment, the first non-cutting portion 23 has a relatively uniform and smooth outer peripheral surface having a constant outer diameter along the axial direction. Therefore, the first non-cutting portion 23 has the constant maximum radius c in the axial direction on the outer peripheral surface. The outer peripheral surface of the first non-cutting portion 23 has a relatively smooth circular shape in the axially orthogonal cross section. In accordance with an exemplary embodiment, the outer diameter of the first non-cutting portion 23 may be changed along the axial direction. For example, the outer diameter of the first non-cutting portion 23 may decrease in a tapered shape toward the distal side. Alternatively, the outer diameter of the first non-cutting portion 23 may decrease in a tapered shape toward the proximal side. Alternatively, the axial center portion of the first non-cutting portion 23 may have the maximum radius c of the first non-cutting portion 23. In accordance with an exemplary embodiment, the axial length L1 of the first non-cutting portion 23 is smaller than the axial length L2 of the second cutting portion 22. Therefore, when the stenosed site S is cut by the second cutting portion 22, it is possible to stabilize a position where the rotating first non-cutting portion 23 comes into contact with the biological tissue.

The second non-cutting portion 24 is located on the proximal side of the second cutting portion 22. In accordance with an exemplary embodiment, the proximal portion of the second non-cutting portion 24 is interlocked (i.e., connected) with the drive shaft 30. The second non-cutting portion 24 can have a relatively uniform and smooth outer peripheral surface having a relatively constant outer diameter along the axial direction. Therefore, the second non-cutting portion 24 has a relatively constant maximum radius d in the axial direction on the outer peripheral surface. The outer peripheral surface of the second non-cutting portion 24 has a relatively smooth circular shape in the axially orthogonal cross section. In accordance with an exemplary embodiment, the outer diameter of the second non-cutting portion 24 may be changed along the axial direction. For example, the outer diameter of the second non-cutting portion 24 may decrease in a tapered shape toward the distal side. Alternatively, the outer diameter of the second non-cutting portion 24 may decrease in a tapered shape toward the proximal side. Alternatively, a substantially axial center portion of the second non-cutting portion 24 may have the maximum radius d of the second non-cutting portion 24.

In accordance with an exemplary embodiment, the maximum radius b of the outer peripheral surface of the above-described second cutting portion 22 is larger than the maximum radius a of the outer peripheral surface of the first cutting portion 21. The maximum radius b of the second cutting portion 22 is also the maximum radius of the structure 20. In addition, the second cutting portion 22 can be located more proximal than the first cutting portion 21. Therefore, after the stenosed site S can be shallowly cut by the first cutting portion 21, the stenosed site S can be deeply cut by the second cutting portion 22 having the larger outer diameter than the first cutting portion 21. Therefore, the cutting portion includes the first cutting portion 21 and the second cutting portion 22, and wherein the first non-cutting portion 23 is interposed or placed between the first cutting portion 21 and the second cutting portion 22. Accordingly, the cutting portion cuts the stenosed site S in a stepwise manner. In this manner, while safety is relatively ensured, the stenosed site S can be deeply cut at a final stage.

In accordance with an exemplary embodiment, the maximum radius b of the outer peripheral surface of the second cutting portion 22 can be larger than the maximum radius c of the outer peripheral surface of the first non-cutting portion 23. In addition, the maximum radius b of the outer peripheral surface of the second cutting portion 22 is equal to or larger than the maximum radius d of the outer peripheral surface of the second non-cutting portion 24. According to the present embodiment, the maximum radius b of the outer peripheral surface of the second cutting portion 22 is larger than the maximum radius d of the outer peripheral surface of the second non-cutting portion 24. Therefore, the second cutting portion 22 protrudes outward in the radial direction between the first non-cutting portion 23 and the second non-cutting portion 24. Accordingly, the second cutting portion 22 can be provided with improved cutting capacity.

In accordance with an exemplary embodiment, the maximum radius d of the outer peripheral surface of the second non-cutting portion 24 can be larger than the maximum radius c of the outer peripheral surface of the first non-cutting portion 23. The second non-cutting portion 24 is located more proximal than the first non-cutting portion 23. Therefore, as a first cutting stage, while the first non-cutting portion 23 is brought into contact with the biological tissue, the object can be cut rather shallowly by the first cutting portion 21. Thereafter, as a second cutting stage, while the second non-cutting portion 24 having the larger maximum radius than the first non-cutting portion 23 is brought into contact with the biological tissue, the stenosed site S can be cut rather deeply by the second cutting portion 22 having the larger maximum radius than the first cutting portion 21.

Then, in accordance with an exemplary embodiment, the structure 20 satisfies Equation (1), Equation (2), and Equation (3) below.

$$a<d\leq b \qquad \text{Equation (1)}$$

$$L1<L2 \qquad \text{Equation (2)}$$

$$a-100\ \mu m \leq c<b \qquad \text{Equation (3)}$$

That is, the maximum radius a of the first cutting portion 21 is smaller than the maximum radius d of the second non-cutting portion 24. In addition, the maximum radius b of the second cutting portion 22 is larger than the maximum radius d of the second non-cutting portion 24. In addition, the axial length L1 of the first non-cutting portion 23 is smaller than the axial length L2 of the second cutting portion 22. In addition, the maximum radius c of the first non-cutting portion 23 is equal to or greater than a value obtained by subtracting the maximum protruding amount P (100 μm) of the abrasive grains 72 from the maximum radius a of the first cutting portion 21. That is, the maximum radius a including the abrasive grains 72 of the first cutting portion 21 may be larger than the maximum radius c of the first non-cutting portion 23 as much as the amount of the abrasive grains 72. As described above, the maximum protruding amount P of the abrasive grains 72 can be, for example, 100 μm. However, the maximum protruding amount P is more preferably, for example, 50 μm, still more preferably 30 μm, and further still more preferably 20 μm. In addition, the maximum radius b of the second cutting portion 22 can be larger than the maximum radius of the first non-cutting portion 23. The significance of satisfying each equation will be described in detail later in a usage example of the medical device 10.

In accordance with an exemplary embodiment, a portion of the second cutting portion 22 deviates outward in the radial direction from a tangent T to the first non-cutting portion 23 and the second non-cutting portion 24 in a cross section along the axial direction. In the cross section along the axial direction of the structure 20, a deviation distance e from the tangent T to the most distant portion 29, which is most distant in a direction perpendicular to the tangent T and away from the central axis of the structure 20 satisfies Equation (4) below. In accordance with an exemplary embodiment, the most distant portion 29 of the second cutting portion 22 is located at a boundary between the outer peripheral surfaces of the diameter decreasing portion 26 and the uniform diameter portion 27. The tangent T to the first non-cutting portion 23 and the second non-cutting portion 24 in the cross section along the axial direction means a straight line located most distant from the central axis, among the straight lines in contact with both the first non-cutting portion 23 and the second non-cutting portion 24.

$$a-ai+e<b \qquad \text{Equation (4)}$$

In addition, the first cutting portion 21 is located inward in the radial direction from the tangent T or on the tangent T to the first non-cutting portion 23 and the second non-cutting portion 24 in the cross section along the axial direction.

In addition, the medical device 10 satisfies Equation (5) and Equation (6) below. Since Equation (5) is satisfied, the outer diameter of the second non-cutting portion 24 becomes larger than the outer diameter of the first non-cutting portion 23. Therefore, the medical device 10 can freely pass through the blood vessel. Incidentally, the thickness of the vascular wall can be generally thicker than, for example, 20 μm, and is thinner than, for example, 150 μm. Therefore, since Equation (6) is satisfied, the deviation distance e becomes smaller than the maximum value (150 μm) of the thickness of the vascular wall. Accordingly, the vascular wall can be prevented from being excessively cut by the second cutting portion 22, thereby improving the relative safety of the medical device 10. The deviation distance e may be smaller than the minimum value (20 μm) of the thickness of the vascular wall. In this case, the vascular wall can be further prevented from being excessively cut by the second cutting portion 22, thereby further improving the relative safety.

$$c<d \qquad \text{Equation (5)}$$

$$e<150\ \mu m \qquad \text{Equation (6)}$$

The material of the structure 20 is not particularly limited. For example, the structure 20 material can be stainless steel, CoCr, NiCr, brass, WC, tantalum (Ta), titanium (Ti), platinum (Pt), gold (Au), tungsten (W), polyolefin such as polyethylene and polypropylene, polyester such as polyamide and polyethylene terephthalate, fluorine-based polymer such as tetrafluoroethylene-ethylene copolymer (ETFE), polyether ether ketone (PEEK), or polyimide.

The maximum outer diameter of the structure 20 can be appropriately selected depending on the inner diameter of the biological lumen in which the medical device 10 can be used. For example, the maximum outer diameter of the structure 20 can be 0.5 mm to 10.0 mm. As an example, the maximum outer diameter of the structure 20 can be 2.0 mm.

As illustrated in FIGS. 1 and 2, the drive shaft 30 is formed in a tubular shape. In accordance with an exemplary embodiment, the distal side is fixed to the proximal end portion of the structure 20, and a driven gear 31 is fixed to the proximal side. The proximal portion of the drive shaft 30 is rotatably interlocked (i.e., connected) with a casing 41 of the operation unit 40.

In accordance with an exemplary embodiment, the drive shaft 30 is not only flexible, but also capable of transmitting rotational power acting from the proximal side to the distal side. For example, the drive shaft 30 includes a single-layer coil, a multilayer coil or tubular body such as a three-layer coil with alternate rightward, leftward, and rightward winding directions, or a material including polyolefin such as polyethylene or polypropylene, polyamide, polyester such as polyethylene terephthalate, fluoropolymer such as tetrafluoroethylene-ethylene copolymer (ETFE), polyether ether ketone (PEEK), polyimide, or any combination of materials and a reinforcing member, such as a wire, embedded in the material(s) of the drive shaft 30.

In accordance with an exemplary embodiment, the inner diameter of the drive shaft 30 can be appropriately selected. For example, the inner diameter of the drive shaft 30 can be 0.45 mm to 1.5 mm. As an example, the inner diameter of the drive shaft 30 can be, for example, 0.6 mm. The outer diameter of the drive shaft 30 can be appropriately selected. For example, the outer diameter of the drive shaft 30 can be, for example, 0.8 mm to 1.5 mm. As an example, the outer diameter of the drive shaft 30 can be, for example, 1.2 mm.

In accordance with an exemplary embodiment, the outer sheath 50 is a tubular body which covers the outside of the drive shaft 30, and is movable and rotatable with respect to the drive shaft 30 in the axial direction. The outer sheath 50 can be operated by gripping the proximal portion. The outer sheath 50 can internally accommodate the structure 20 by moving to the distal side with respect to the drive shaft 30. In addition, the outer sheath 50 can expose the structure 20 outward by moving the proximal side with respect to the drive shaft 30. The outer sheath 50 may be a guiding sheath provided separately from the medical device 10.

In accordance with an exemplary embodiment, the material of the outer sheath 50 is not particularly limited. For example, the outer sheath 50 material can be polyolefin such as polyethylene and polypropylene, polyester such as polyamide and polyethylene terephthalate, fluoropolymer such as tetrafluoroethylene-ethylene copolymer (ETFE), polyether ether ketone (PEEK), or polyimide. In addition, the outer sheath 50 may be made of a plurality of materials, or a reinforcing member such as a wire may be incorporated in the material(s) of the outer sheath 50.

The inner diameter of the outer sheath 50 can be appropriately selected. For example, the inner diameter of the outer sheath 50 can be, for example, 1.0 mm to 3.0 mm. As an example, the inner diameter of the outer sheath 50 can be, for example, 2.1 mm. The outer diameter of the outer sheath 50 can be appropriately selected. For example, the outer diameter of the outer sheath 50 can be, for example, 1.2 mm to 4.0 mm. As an example, the outer diameter of the outer sheath 50 can be, for example, 2.5 mm.

In accordance with an exemplary embodiment, the operation unit 40 includes the casing 41, a drive gear 42 meshing with the driven gear 31, and a motor 44 serving as a drive source including a rotary shaft 43 to which the drive gear 42 is fixed. The operation unit 40 further includes a battery 45 such as a battery for supplying electric power to the motor 44 and a switch 46 for controlling the driving of the motor 44. If the switch 46 is turned on, the rotary shaft 43 of the motor 44 and the drive gear 42 are rotated. If the drive gear 42 is rotated, the driven gear 31 meshing with the drive gear 42 is rotated, and the drive shaft 30 is rotated. If the drive shaft 30 is rotated, the structure 20 fixed to the distal side of the drive shaft 30 is rotated, thereby enabling the stenosed site S to be cut.

Figure 4A:
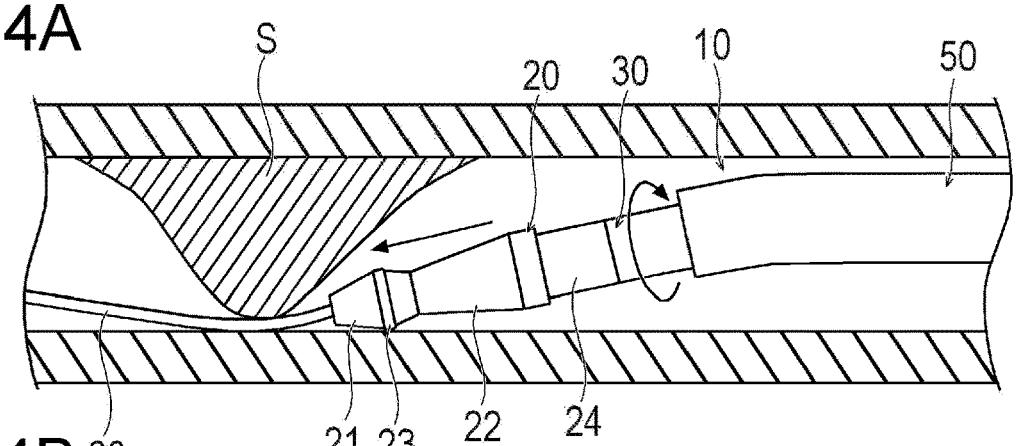
Figure 5:
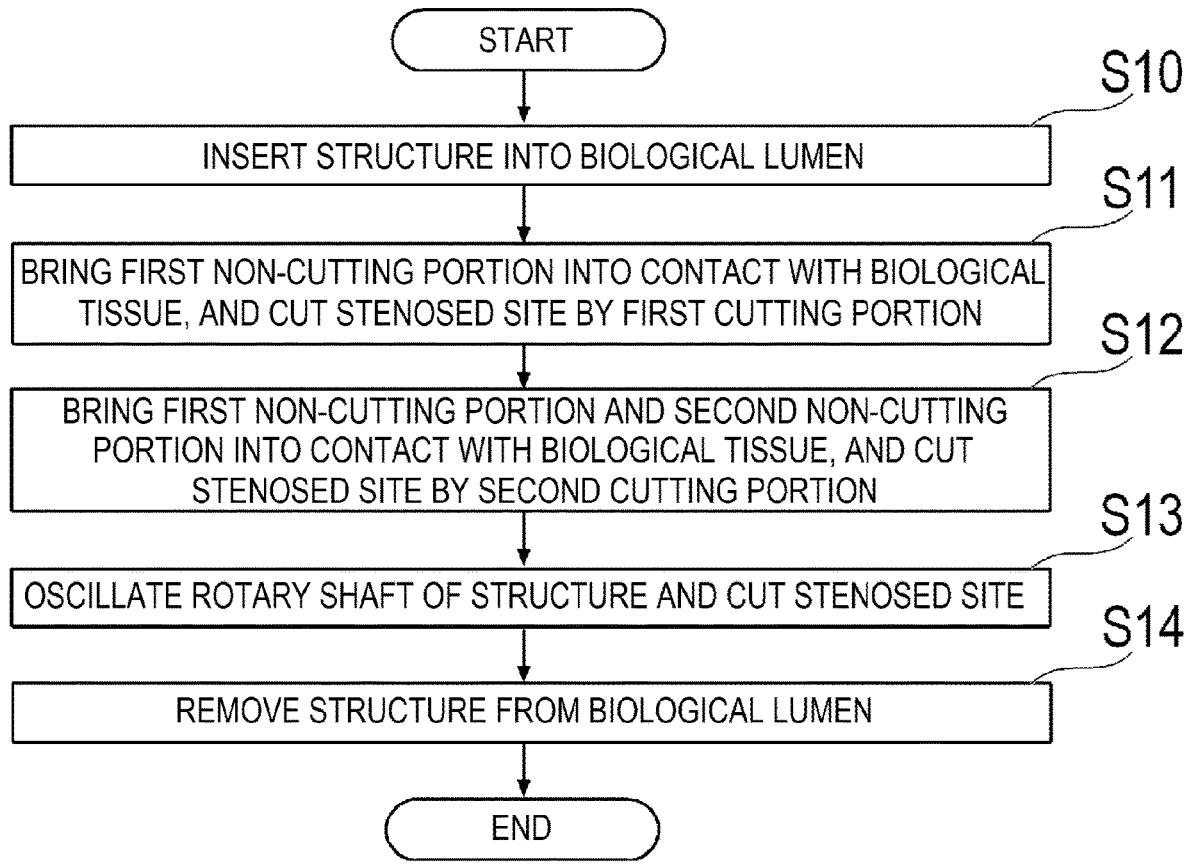
FIG. 5 is a flowchart for describing a medical procedure using the medical device.

Next, with regard to a method of using the medical device 10 according to the present embodiment, as an example, a case of cutting the stenosed site S inside the blood vessel will be described with reference to a flowchart illustrated in FIG. 5. A shape of the stenosed site S is not limited to a symmetrical shape. Accordingly, in some cases, the stenosed site S may be biased in the blood vessel. Here, as illustrated in FIG. 4A, a case where the stenosed site S inside the blood vessel is biased to a portion in the circumferential direction of the vascular wall will be described as an example.

First, an introducer sheath (not illustrated) is percutaneously inserted into the blood vessel on an upstream side (proximal side) of the stenosed site S in the blood vessel. The guide wire 60 is inserted into the blood vessel via an introducer sheath.

Next, the medical device 10 is prepared in a state where the structure 20 is accommodated inside the outer sheath 50. The proximal side end portion of the guide wire 60 is inserted into the distal side opening portion 20A of the structure 20. Subsequently, while the guide wire 60 is moved ahead, the medical device 10 is pushed forward (i.e., in a distal direction). The distal side end portion of the medical device 10 is located on the proximal side of the stenosed site S (Step S10). Next, the outer sheath 50 is moved to the proximal side, and the structure 20 is exposed inside the blood vessel.

Next, if the switch 46 (refer to FIG. 1) of the operation unit 40 is turned on, the driving force of the motor 44 is transmitted from the drive gear 42 to the driven gear 31. Then, the drive shaft 30 interlocked with the driven gear 31 is rotated, and the structure 20 interlocked with the drive shaft 30 is rotated.

Figure 4B:
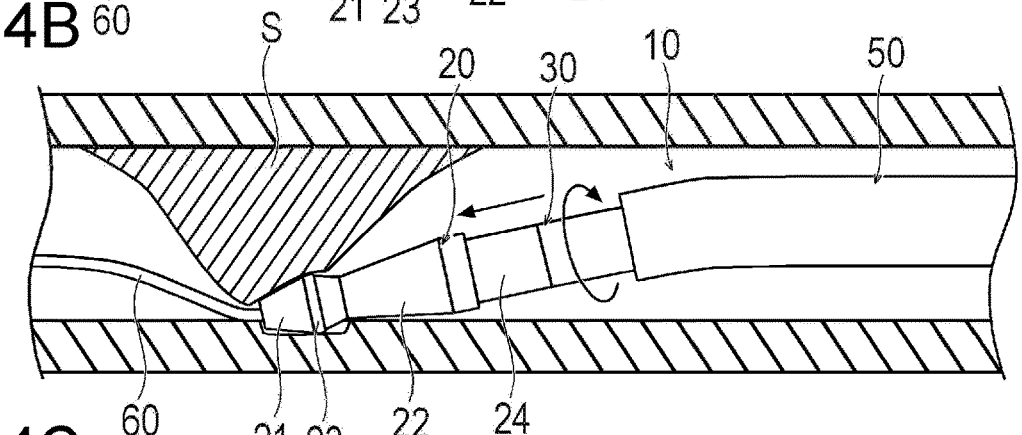

Next, in a state where the structure 20 is rotated, the medical device 10 is pushed forward as illustrated in FIG. 4B. In this manner, the first cutting portion 21 located in the most distal end of the structure 20 comes into contact with the stenosed site S, thereby cutting the stenosed site S. The cut stenosed site S turns into debris, and flows to the distal side (downstream side) inside the blood vessel. In accordance with an exemplary embodiment, the debris flowing inside the blood vessel can be collected by a filter or a balloon separately provided on the downstream side of the blood vessel. In this manner, the debris can be prevented from flowing to a peripheral blood vessel, and a new stenosis can be prevented from appearing in the peripheral blood vessel. Alternatively, the thrombus-type debris formed by cutting the stenosed site S may be dissolved by a thrombus dissolving agent.

In a case where the stenosed site S is biased inside the blood vessel, if the structure 20 is pushed into the blood vessel along the guide wire 60 penetrating the stenosed site S, the structure 20 moves close to the vascular wall while being inclined with respect to the axis of the blood vessel. In this manner, first, the first cutting portion 21 or the first non-cutting portion 23 located at the most distal end of the structure 20 comes into contact with the vascular wall on a side opposite to a side having the stenosed site S. If the first non-cutting portion 23 comes into contact with the vascular wall, the first non-cutting portion 23 comes into relatively smooth contact with the vascular wall. Therefore, the rotation of the structure 20 can be stably maintained, and damage to the vascular wall can be prevented. In addition, if the first cutting portion 21 comes into contact with the vascular wall, the first cutting portion 21 cuts the vascular wall. However, the guide wire 60 is inserted into the guide wire lumen 28 of the structure 20. Therefore, a maximum value of the depth of the vascular wall cut by the first cutting portion 21 is proportional to the maximum radius a of the first cutting portion 21. Specifically, the maximum value of the depth of the vascular wall cut by the first cutting portion 21 is the length in the radial direction in the range where the first cutting portion 21 can perform cutting. That is, for example, the maximum value of the depth of the vascular wall cut by the first cutting portion 21 is a value obtained by subtracting the minimum radius ai from the maximum radius a in a range having the abrasive grains 72 of the first cutting portion 21. In accordance with an exemplary embodiment, the maximum value of the depth of the vascular wall cut by the first cutting portion 21 is smaller than the thickness of the vascular wall, and there is relatively no problem of vascular perforation. That is, for example, the guide wire 60 is led out to the distal side, and the first non-cutting portion 23 is located on the proximal side. Accordingly, even if the first cutting portion 21 is pressed against the vascular wall, a cuttable depth of the vascular wall can be limited. Then, while the first cutting portion 21 pushed into the distal side is interposed (i.e., placed) between the stenosed site S and the vascular wall, the cuttable depth of the vascular wall can be limited. Accordingly, the stenosed site S on the opposite side can be cut relatively effectively.

As illustrated in Equation (1) described above, the maximum radius a of the first cutting portion 21 is smaller than the maximum radius d of the second non-cutting portion 24. Therefore, before the second non-cutting portion 24 is brought into relatively smooth contact with the vascular wall and the stenosed site S is cut relatively deeply by the second cutting portion 22, the stenosed site S can be cut relatively shallowly by the first cutting portion 21.

As illustrated in Equation (3) described above, the maximum radius c of the first non-cutting portion 23 is equal to or larger than the maximum radius a of the first cutting portion 21. Therefore, when the stenosed site S can be cut by the first cutting portion 21, the first non-cutting portion 23 is brought into relatively smooth contact with the vascular wall. In this manner, the vascular wall can be prevented from being damaged by the first cutting portion 21 (Step S11).

Figure 4C:
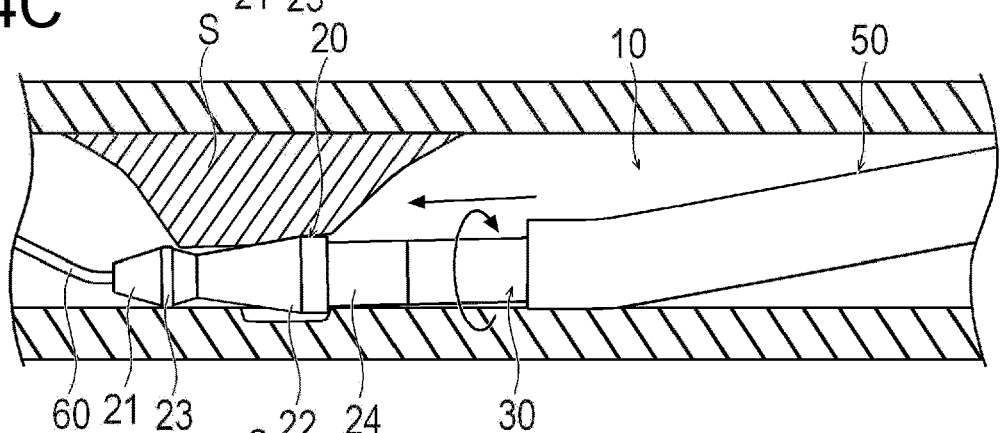

Next, as illustrated in FIG. 4C, while the stenosed site S is cut by the first cutting portion 21, the first cutting portion 21 is pushed into the distal side. As illustrated in Equation (1) described above, the maximum radius b of the second cutting portion 22 is larger than the maximum radius d of the second non-cutting portion 24. Therefore, when the first non-cutting portion 23 is pushed into the distal side, the second cutting portion 22 having the larger outer diameter than the first non-cutting portion 23 can be effectively brought into contact with the stenosed site S. Then, the first non-cutting portion 23 is brought into relatively smooth contact with the vascular wall. In this manner, the vascular wall can be prevented from being damaged by the second cutting portion 22. Therefore, while a relative safety of a living body can be ensured, the stenosed site S can be deeply cut by the second cutting portion 22.

When the first cutting portion 21 and the first non-cutting portion 23 pass through the stenosed site S on the distal side, the first non-cutting portion 23 and the second non-cutting portion 24 come into contact with the vascular wall, and the second cutting portion 22 cuts the stenosed site S (Step S12). When the first cutting portion 21 and the first non-cutting portion 23 pass through the stenosed site S on the distal side, the first cutting portion 21 and the first non-cutting portion 23 do not receive any force from the stenosed site S. Accordingly, the force to press the first cutting portion 21 against the vascular wall can be significantly weakened. Therefore, the first non-cutting portion 23 can be brought into relatively smooth contact with the vascular wall. In this manner, the first cutting portion 21 can be prevented from coming into contact with the vascular wall. In this case, the first cutting portion 21 is located inside the tangent T. Accordingly, the vascular wall can be relatively effectively prevented from being damaged by the first cutting portion 21.

As illustrated in Equation (3) described above, the maximum radius b of the second cutting portion 22 is larger than the maximum radius a of the first cutting portion 21 and the maximum radius c of the first non-cutting portion 23. Therefore, the stenosed site S cut relatively shallow by the first cutting portion 21 can be cut relatively deeply by the second cutting portion 22. The second cutting portion 22 has the most distant portion 29 protruding outward from the tangent T to the first non-cutting portion 23 and the second non-cutting portion 24. Therefore, the most distant portion 29 can cut the vascular wall. The maximum value of the depth of the vascular wall cut by the second cutting portion 22 in a state where the first non-cutting portion 23 and the second non-cutting portion 24 are in contact with the vascular wall coincides with the deviation distance e from the tangent T to most distant portion 29. Therefore, a sum of the cutting depth of the vascular wall cut by the first cutting portion 21 and the cutting depth of the vascular wall cut by the second cutting portion 22 is the sum of the deviation distance e and the value obtained by subtracting the minimum radius $a_i$ from the maximum radius a in the range where the first cutting portion 21 can perform cutting. As illustrated in Equation (4) described above, the total value $(a-a_i+e)$ (i.e., $((a-a_i)+e)$) is smaller than the maximum radius b of the second cutting portion 22. Therefore, while cutting efficiency of the stenosed site S can be improved by the second cutting portion 22 having the larger outer diameter of the maximum radius b, the cutting depth of the vascular wall can be set to $(a-a_i+e)$, which is smaller than the maximum radius b of the second cutting portion 22. Therefore, the damage to the vascular wall can be reduced. In addition, the second cutting portion 22 has a portion deviating outward in the radial direction from the tangent T. Accordingly, compared to a case where the portion does not deviate outward in the radial direction from the tangent T, the stenosed site S can be cut relatively effectively. The total value $(a-a_i+e)$ of the cutting depth of the vascular wall which may be cut by the first cutting portion 21 and the second cutting portion 22 is smaller than the thickness of the vascular wall. Therefore, there is relatively no problem of vascular perforation. In accordance with an exemplary embodiment, the total value $(a-a_i+e)$ is preferably, for example, smaller than 1000 μm, more preferably smaller than 500 μm, and still more preferably smaller than 250 μm. In this manner, the vascular perforation caused by the first cutting portion 21 and the second cutting portion 22 can be prevented.

In addition, as illustrated in Equation (2) described above, the axial length L1 of the first non-cutting portion 23 is smaller than the axial length of the second cutting portion 22. Therefore, when the stenosed site S is cut by the second cutting portion 22, a position where the rotating first non-cutting portion 23 comes into contact with the vascular wall is stabilized, and the rotating structure 20 can be stably supported by the first non-cutting portion 23. The rotating structure 20 can be stably supported by the first non-cutting portion 23. Accordingly, the medical device 10 can cut relatively effectively the stenosed site S inside the biological lumen, and the safety can be relatively improved by reducing the damage to the vascular wall.

Figure 4D:
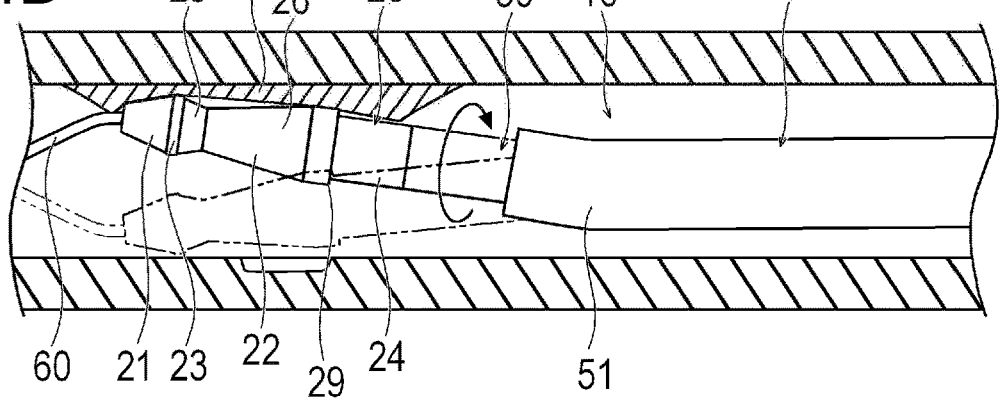

Next, the operation unit 40 and the outer sheath 50 are rotationally operated, and the rotary shaft 43 of the structure 20 is caused to oscillate as illustrated in FIG. 4D. In this manner, while a risk of the damage to the vascular wall can be reduced by the first non-cutting portion 23 and the second non-cutting portion 24 which come into relatively smooth contact with the vascular wall, the stenosed site S can be effectively and largely cut by the second cutting portion 22 or the first cutting portion 21 and the second cutting portion 22. In a case where a bent portion 51 bent at a predetermined angle is formed in the distal portion of the outer sheath 50, the outer sheath 50 is rotated, and the direction of the distal portion of the outer sheath 50 can be changed. In this manner, the rotary shaft 43 of the structure 20 can be caused to oscillate (Step S13).

Thereafter, the rotation, the oscillation, and forward/rearward movement of the structure 20 can be repeated. In this manner, while the damage to the vascular wall can be prevented by the first non-cutting portion 23 and the second non-cutting portion 24, the stenosed site S can be cut relatively effectively by the first cutting portion 21 and the second cutting portion 22. In accordance with an exemplary embodiment, the diameter of the first cutting portion 21 and the diameter decreasing portion 26 decreases toward the distal side. Accordingly, the stenosed site S can be cut relatively effectively when the medical device 10 is pushed into the distal side. The diameter of the diameter increasing portion 25 decreases toward the proximal side. Accordingly, the stenosed site S can be cut relatively effectively when the medical device 10 is pulled to the proximal side.

In accordance with an exemplary embodiment, after the stenosed site S is completely cut, the switch 46 is turned off so as to stop the rotation of the drive shaft 30. Thereafter, the outer sheath 50 is moved to the distal side, or the structure 20 is moved to the proximal side so that the structure 20 is accommodated inside the outer sheath 50. Thereafter, the outer sheath 50 is left behind, and the structure 20 and the drive shaft 30 are removed from the body (Step S14).

Next, a syringe is connected to the proximal side of the outer sheath 50 via a Y-connector. Thereafter, if a plunger of the syringe is pulled to apply an aspiration force, the debris formed by cutting the stenosed site S can be aspirated into the syringe via a lumen of the outer sheath 50. An instrument for aspirating the debris may not be the outer sheath 50, and may be other catheters. In addition, an instrument for applying the aspiration force is not limited to the syringe, and may be a pump, for example. In addition, the debris may not be aspirated and discharged out of the body. The debris may be collected into the sheath inserted into the blood vessel by a filter or a balloon, for example.

Thereafter, the outer sheath 50 is removed, and the introducer sheath is removed, thereby completing the medical procedure.

As described above, there is provided the medical device 10 for cutting the stenosed site S (object) inside the biological lumen according to the present embodiment. In accordance with an exemplary embodiment, the medical device 10 includes the rotatable drive shaft 30, and the structure 20 that is interlocked with the distal portion of the drive shaft 30 and rotatable by the drive shaft 30. The structure 20 has the cutting portion capable of cutting the stenosed site S, and the non-cutting portion having the outer peripheral surface smoother than the cutting portion with respect to the biological tissue. The cutting portion has the first cutting portion 21 and the second cutting portion 22 located more proximal than the first cutting portion 21. The non-cutting portion has the first non-cutting portion 23 located between the first cutting portion 21 and the second cutting portion 22. The structure 20 has the second non-cutting portion 24 located on the proximal side of the second cutting portion 22. In accordance with an exemplary embodiment, the structure 20 satisfies all of Equations (A) to (E) below wherein a represents the maximum radius of the outer peripheral surface of the first cutting portion 21, b represents the maximum radius of the outer peripheral surface of the second cutting portion 22, c represents the maximum radius of the outer peripheral surface of the first non-cutting portion 23, d represents the maximum radius of the outer peripheral surface of the second non-cutting portion 24, L1 represents the axial length of the first non-cutting portion 23, and L2 represents the axial length of the second cutting portion 22.

$$a<b \quad \text{Equation (A)}$$

$$c<d \quad \text{Equation (B)}$$

$$d \leq b \quad \text{Equation (C)}$$

$$a<d \quad \text{Equation (D)}$$

$$L1<L2 \quad \text{Equation (E)}$$

The medical device 10 configured as described above has the first cutting portion 21 and the second cutting portion 22, and wherein the first non-cutting portion 23 is interposed or placed between the first cutting portion 21 and the second cutting portion 22. Accordingly, the medical device 10 cuts the stenosed site S in a stepwise manner. In this manner, while the safety can be relatively ensured, the stenosed site S can be cut relatively deeply (largely) at a final stage. In accordance with an exemplary embodiment, the medical device 10 satisfies Equation (A) and Equation (D), and has the first cutting portion 21 having the maximum radius a smaller than the maximum radius b of the second cutting portion 22 and the maximum radius d of the second non-cutting portion 24 and located more distal than the first non-cutting portion 23. Accordingly, before the stenosed site S is cut relatively deeply by the second cutting portion 22, the stenosed site S can be cut by the first cutting portion 21 while the damage to the biological tissue can be prevented by the first non-cutting portion 23. In addition, the medical device 10 satisfies Equation (A) and Equation (C), and the second cutting portion 22 including the maximum radius b larger than the maximum radius a of the first cutting portion 21 and equal to or larger than the maximum radius d of the second non-cutting portion 24 can more cut relatively deeply the stenosed site S inside the biological lumen than the first cutting portion 21. Then, the second cutting portion 22 can be interposed (i.e., placed) between the first non-cutting portion 23 and the second non-cutting portion 24. Accordingly, the biological tissue can be prevented from being excessively damaged by the second cutting portion. Improved cutting capacity and improved safety can be compatibly achieved. Furthermore, Equation (E) is satisfied, and the axial length L1 of the first non-cutting portion 23 is smaller than the axial length L2 of the second cutting portion 22. Accordingly, when the stenosed site S is cut by the second cutting portion 22, a position where the rotating first non-cutting portion 23 comes into contact with the biological tissue is stabilized. Therefore, the rotating structure 20 can be stably supported by the first non-cutting portion 23, and the improved cutting capacity and safety can be maintained. Therefore, according to the medical device 10, the stenosed site S inside the biological tissue can be cut relatively effectively, and the safety can be improved by reducing the damage to the biological tissue. Equation (B) is satisfied, and the maximum radius c of the first non-cutting portion 23 is smaller than the maximum radius d of the second non-cutting portion 24. Therefore, the medical device 10 can freely pass through the blood vessel.

In addition, the medical device 10 satisfies Equation (F) below. In this manner, the maximum radius c of the outer peripheral surface of the first non-cutting portion 23 is at least the value obtained by subtracting the maximum protruding amount P (for example, 100 µm) of the abrasive grains 72 from the maximum radius a of the outer peripheral surface of the first cutting portion 21. Accordingly, after the stenosed site S is cut by the first cutting portion 21, the first cutting portion 21 is pushed into the distal side so as to bring the first non-cutting portion 23 into contact with the biological tissue. In this manner, the biological tissue can be prevented from being excessively cut by the first cutting portion 21. In addition, the maximum radius b of the outer peripheral surface of the second cutting portion 22 is larger than the maximum radius c of the outer peripheral surface of the first non-cutting portion 23. Accordingly, after the stenosed site S is cut relatively shallow by the first cutting portion 21, the first non-cutting portion 23 is pushed into the distal side. In this manner, the second cutting portion 22 having the larger outer diameter than the first cutting portion 21 and the first non-cutting portion 23 can be effectively brought into the stenosed site S. Then, the first non-cutting portion 23 is brought into relatively smooth contact with the biological tissue. While the biological tissue can be prevented from being damaged by the first cutting portion 21 and the second cutting portion 22, the stenosed site S can be cut relatively deeply by the second cutting portion 22.

$$a-100\ \mu m \le c < b \quad \text{Equation (F)}$$

In addition, the medical device 10 satisfies Equation (G) described above, wherein e represents the deviation distance from the tangent T to the first non-cutting portion 23 and the second non-cutting portion 24 to the most distant portion 29 of the second cutting portion 22 most distant in the direction perpendicular to the tangent T and away from the central axis of the structure 20 in the cross section along the axial direction of the structure 20. In this manner, the depth of the biological tissue which may be damaged by the first cutting portion 21 is the value obtained by subtracting the minimum radius ai from the maximum radius a. After the biological tissue is cut by the first cutting portion 21, the first non-cutting portion 23 and the second non-cutting portion 24 are brought into the biological tissue. In this way, the depth of the biological tissue which can be damaged by the second cutting portion 22 is the deviation distance e. Then, the total value (a-ai+e) of the depth of the biological tissue which may be damaged by both the first cutting portion 21 and the second cutting portion 22 is smaller than the maximum radius b of the outer peripheral surface of the second cutting portion 22. Therefore, while the cutting efficiency of the stenosed site S can be improved by the second cutting portion 22 having the larger outer diameter of the maximum radius c, the cutting depth of the vascular wall can be set to (a-ai+e), which is smaller than the maximum radius c of the first non-cutting portion 23. Therefore, the damage to the vascular wall can be reduced.

$$a-ai+e<b \quad \text{Equation (G)}$$

In addition, the second cutting portion 22 has the diameter decreasing portion 26 whose outer diameter decreases in a tapered shape toward the distal side. In this manner, the stenosed site S can be effectively cut by the diameter decreasing portion 26 by performing an operation of pushing the second cutting portion 22 into the distal side.

In addition, the second cutting portion 22 has the diameter increasing portion 25 whose outer diameter increases in a tapered shape toward the distal side. In this manner, the stenosed site S can be effectively cut by the diameter increasing portion 25 by performing an operation of pulling the second cutting portion 22 to the proximal side.

In addition, the outer diameter of at least a portion of the first cutting portion 21 decreases in a tapered shape toward the distal side. In this manner, the stenosed site S can be effectively cut by the first cutting portion 21 by performing the operation of pushing the first cutting portion 21 into the distal side.

In accordance with an exemplary embodiment, the structure 20 is a rigid body. In this manner, a positional relationship is not changed between the cutting portion and the non-cutting portion. Accordingly, the damage to the biological tissue which is caused by the first cutting portion 21 and the second cutting portion 22 can be properly minimized within a preset range by the first non-cutting portion 23 and the second non-cutting portion 24. In accordance with an aspect, the structure 20 may not be a rigid body. That is, for example, the positional relationship among the first cutting portion 21, the first non-cutting portion 23, the second cutting portion 22, and the second non-cutting portion 24 may be changed to some extent during the process of cutting the stenosed site S. Therefore, in the structure 20, the range including the first cutting portion 21, the first non-cutting portion 23, the second cutting portion 22, and the second non-cutting portion 24 may be set so that the structure 20 can be bent.

In addition, there is provided the medical device 10 for cutting the stenosed site S (object) inside the biological lumen according to the present embodiment. The medical device 10 includes the rotatable drive shaft 30, and the structure 20 interlocked with the distal portion of the drive shaft 30 and rotated by the drive shaft 30. The structure 20 has the cutting portion capable of cutting the stenosed site S, and the non-cutting portion having the outer peripheral surface smoother than the cutting portion with respect to the biological tissue. The non-cutting portion has the first non-cutting portion 23 located on the distal side of the cutting portion. The structure 20 has the second non-cutting portion 24 located on the proximal side of the cutting portion. Equations (B) and (H) below are satisfied, wherein c represents the maximum radius of the outer peripheral surface of the first non-cutting portion 23, d represents the maximum radius of the outer peripheral surface of the second non-cutting portion 24, and e represents the deviation distance from the tangent T to the first non-cutting portion 23 and the second non-cutting portion 24 to the most distant portion 29 of the cutting portion, which is most distant in the direction perpendicular to the tangent T and away from the central axis of the structure 20 in the cross section along the axial direction of the structure 20. Since Equation (B) is satisfied, the outer diameter of the second non-cutting portion 24 becomes relatively larger than the outer diameter of the first non-cutting portion 23. Therefore, the medical device 10 can freely pass through the blood vessel. Furthermore, since Equation (H) is satisfied, the deviation distance e becomes smaller than the thickness of the vascular wall. Therefore, the safety of the medical device 10 can be improved.

$$c<d \quad \text{Equation (B)}$$

$$e<150\ \mu m \quad \text{Equation (H)}$$

In addition, the cutting portion has the first cutting portion 21 and the second cutting portion 22 located more proximal than the first cutting portion. The first cutting portion 21 is located on the distal side of the first non-cutting portion 23, and the second cutting portion 22 is located on the distal side of the second non-cutting portion 24, which is the proximal side of the first non-cutting portion 23. In this manner, after the cutting is performed by the first cutting portion 21, the first non-cutting portion 23 and the second non-cutting portion 24 can be brought into contact with the biological tissue. In this way, the depth of the biological tissue which may be damaged by the second cutting portion 22 becomes the deviation distance e (for example, smaller than 150 μm). Therefore, the damage of the vascular wall which is caused by the second cutting portion 22 becomes smaller than the thickness of the vascular wall. Therefore, the safety of the medical device 10 can be improved.

In addition, the cutting portion has the second cutting portion 22 located on the distal side of the second non-cutting portion 24, which is the proximal side of the first non-cutting portion 23. The second cutting portion 22 has the distal cutting portion 22A including a portion whose outer diameter increases toward the distal side, and the proximal cutting portion 22B including a portion located on the distal side of the second non-cutting portion 24, which is the proximal side of the distal cutting portion 22A and whose outer diameter decreases toward the distal side. The distal cutting portion 22A is located closer to the central axis of the structure 20 than the tangent T in the direction perpendicular to the tangent T and toward the central axis, and the most distant portion 29 is located in the proximal cutting portion 22B. In this manner, the stenosed site S (object) can be cut by the distal cutting portion 22A and the proximal cutting portion 22B in a stepwise manner. In this manner, while the safety can be relatively ensured, the object can be cut relatively deeply (largely) at a final stage.

In addition, according to the present disclosure, there is also provided the treatment method (medical treatment method) for cutting the stenosed site S (object) inside the biological lumen. There is provided the treatment method for cutting the stenosed site S inside the biological lumen by using the above-described medical device 10. The treatment method has a step of inserting the structure 20 into the biological lumen (Step S10), a step of moving the structure 20 to the distal side while rotating the structure 20, bringing the first non-cutting portion 23 into smooth contact with the biological tissue, and causing the first cutting portion 21 to cut the stenosed site S (Step S11), a step of moving the structure 20 to the distal side, bringing the first non-cutting portion 23 and the second non-cutting portion 24 into contact with the biological tissue, and causing the second cutting portion 22 to cut the stenosed site S by rotating the structure 20 (Step S12), and a step of removing the structure 20 from the inside of the biological lumen (Step S14).

According to the treatment method configured as described above, the first non-cutting portion 23 is brought into relatively smooth contact with the biological tissue, and the stenosed site S can be cut by the first cutting portion 21. Accordingly, before the stenosed site S is cut relatively deeply by the second cutting portion 22, the stenosed site S can be cut relatively shallowly by the first cutting portion 21 while the damage to the biological tissue can be prevented by the first non-cutting portion 23. Then, after the structure 20 is moved to the distal side, while the damage to the biological tissue can be prevented by the first non-cutting portion 23 and the second non-cutting portion 24, and wherein the second cutting portion 22 is interposed (i.e., placed) between the first non-cutting portion 23 and the second non-cutting portion 24, the stenosed site S can be effectively cut by the second cutting portion 22 having the larger outer diameter than the first cutting portion 21. Therefore, according to the treatment method, the stenosed site S inside the biological lumen can be effectively cut. The safety can be improved by reducing the damage to the biological tissue.

In addition, according to the treatment method, in the step of causing the second cutting portion 22 to cut the stenosed site S, the stenosed site S is cut while rotating the structure 20 so that the central axis of the structure 20 oscillates inside the biological lumen (Step S13). In this manner, while the damage to the biological tissue can be prevented by the first non-cutting portion 23 and the second non-cutting portion 24 of the oscillating structure 20, the stenosed site S can be effectively cut by the first cutting portion 21 and the second cutting portion 22.

The present disclosure is not limited to the above-described embodiment, and can be modified in various ways by those skilled in the art within the technical concept of the present invention. For example, the biological lumen into which the medical device 10 is inserted is not limited to the blood vessel. For example, the biological lumen may be a vessel, a ureter, a bile duct, a fallopian tube, or a hepatic duct. In addition, the stenosed site S to be cut is not limited to those which are biased in the circumferential direction of the blood vessel.

Figure 6:
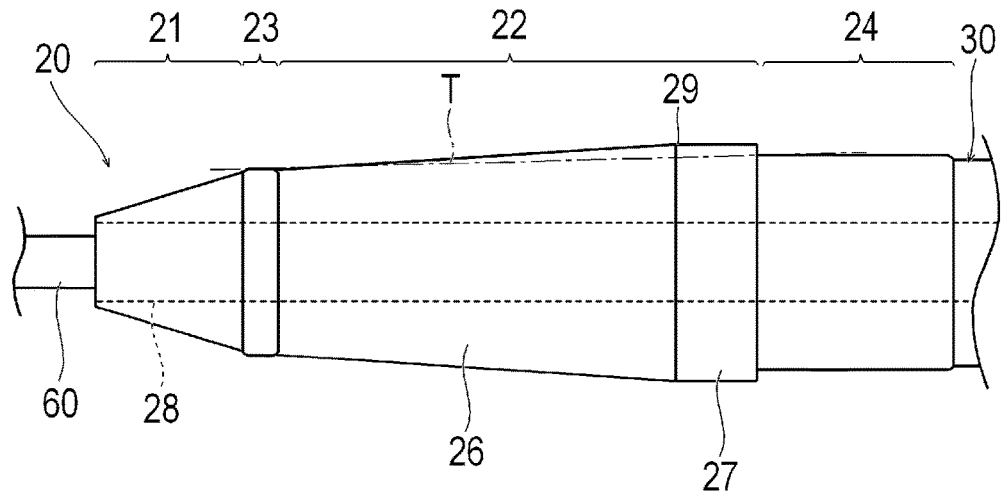
FIG. 6 is a plan view illustrating a modification example of the medical device.
Figure 7:
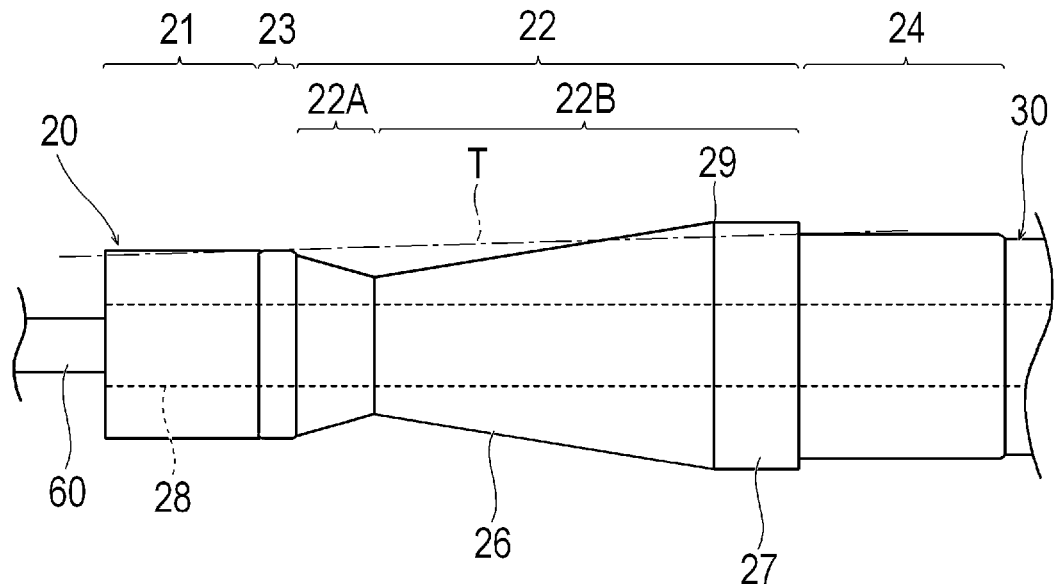
FIG. 7 is a plan view illustrating another modification example of the medical device.

In addition, as in a modification example illustrated in FIG. 6, the second cutting portion 22 may not have the diameter increasing portion 25 whose outer diameter increases in a tapered shape toward the distal side. In addition, as in another modification example illustrated in FIG. 7, the outer diameter of the first cutting portion 21 may be constant along the axial direction. In this case, a portion of the first cutting portion 21 may be located outward in the radial direction from the tangent T to the first non-cutting portion 23 and the second non-cutting portion 24 in the cross section along the axial direction of the structure 20.

Figure 8:
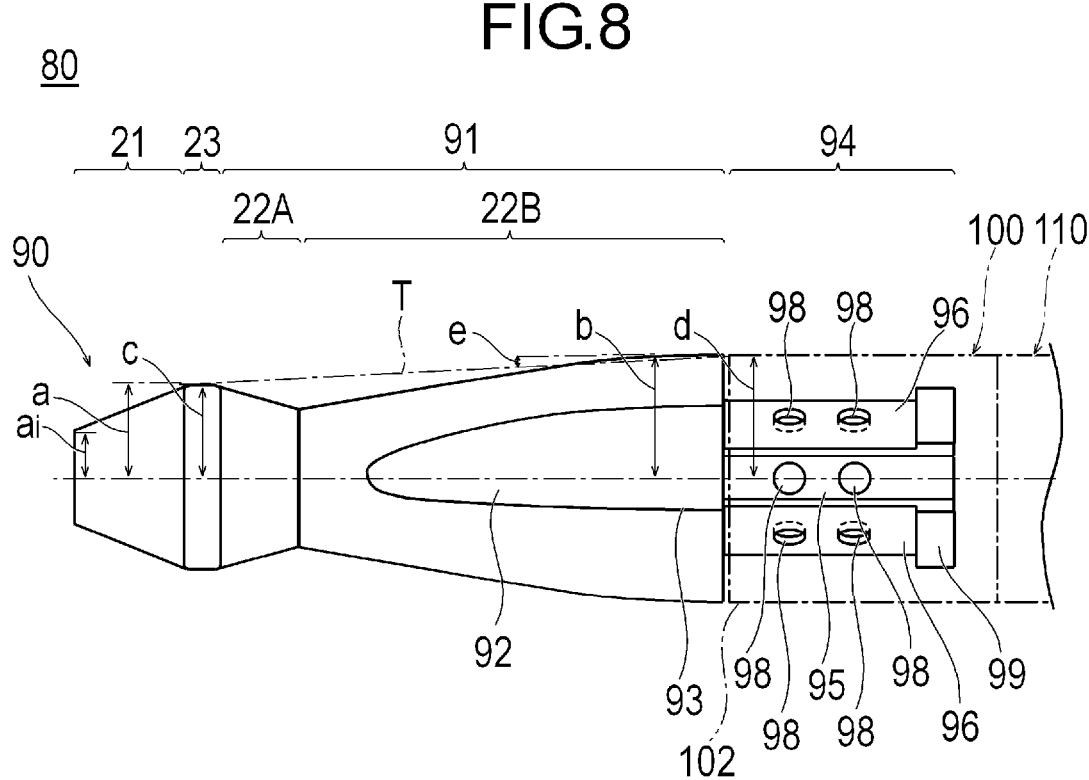
FIG. 8 is a plan view illustrating still another modification example of the medical device.
Figure 9:
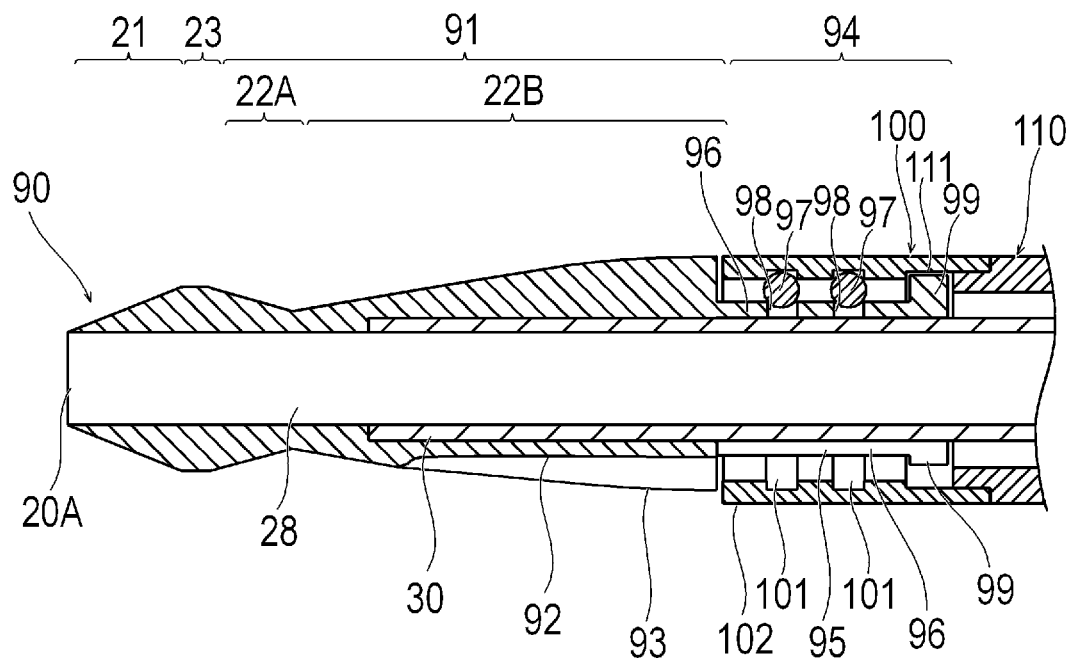
FIG. 9 is a sectional view illustrating still another modification example of the medical device.
Figure 10:
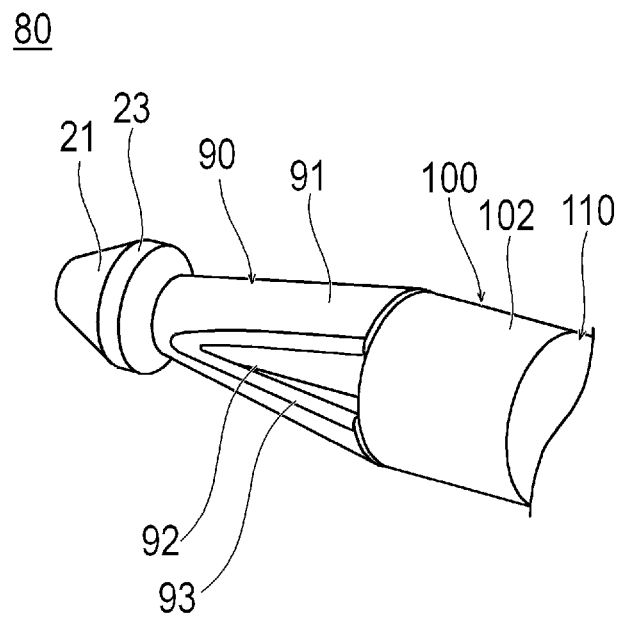
FIG. 10 is a perspective view illustrating still another modification example of the medical device.

In addition, as in still another modification example illustrated in FIGS. 8 to 10, a second non-cutting portion 102 of a medical device 80 may be disposed in a non-rotating tubular body (bearing portion 100) located on the proximal side of a second cutting portion 91. The same reference numerals will be given to elements having the same functions as those according to the above-described embodiment, and description of reference numbers and functions will be omitted. In accordance with an exemplary embodiment, the medical device 80 includes a rotatable structure 90, a drive shaft 30 for rotating the structure 90, an operation unit 40 disposed on an operator's hand side, and an outer sheath 50 capable of accommodating the structure 90. The medical device 80 further includes a bearing portion 100 rotatably supporting the structure 90 and an outer tube 110 rotatably covering the drive shaft 30.

In accordance with an exemplary embodiment, the structure 90 has a first cutting portion 21, a second cutting portion 91, a first non-cutting portion 23, and a support portion 94 supported by a bearing. The second cutting portion 91 protrudes outward in the radial direction while having a curvature in a longitudinal cross section passing through the axial center. The outer peripheral surface of the second cutting portion 91 has a cutout portion 92 cut out in a substantially V-shape in the axially orthogonal cross section. That is, for example, the outer peripheral surface of the second cutting portion 91 may not have a circular shape in the axially orthogonal cross section. In the present embodiment, the cutout portions 92 can be disposed, for example, at every 120 degrees in the circumferential direction. Therefore, the structure 90 has three cutout portions 92 equally juxtaposed with each other in the circumferential direction. In accordance with an exemplary embodiment, an edge portion 93 of the respective cutout portions 92 can be smoothly formed to have a curvature. In addition, the number of the cutout portions 92 is not limited to three. In addition, the cutout portion 92 may be formed in the first cutting portion 21.

In accordance with an exemplary embodiment, the support portion 94 can be rotatably supported by the bearing portion 100. The support portion 94 has three slits 95 located on the proximal side of the three cutout portions 92. The slits 95 extend along the axial direction. The support portion 94 includes three divided support portions 96 interposed (i.e., placed) between the slits 95 and juxtaposed with each other in the circumferential direction. The divided support portions 96 are formed so that one tubular body is divided by the slits 95. Each of the divided support portions 96 has a hole portion 98 capable of accommodating a spherical body 97. The hole portion 98 rotatably accommodates the spherical body 97 which is in contact with the inner peripheral surface of the bearing portion 100. The proximal portion of the divided support portion 96 has an engagement portion 99 protruding outward in the radial direction. In accordance with an exemplary embodiment, the engagement portion 99 can be rotatably fitted into a gap 111 located between the bearing portion 100 and the outer tube 110. Therefore, the structure 90 can be prevented from moving in the axial direction and falling off with respect to the outer tube 110. In the bearing portion 100, a groove portion 101 rotatably supporting the spherical body 97 is formed on the inner peripheral surface of the bearing portion 100. The groove portion 101 extends in the circumferential direction. The bearing portion 100 is interlocked with the distal portion of the outer tube 110. The second non-cutting portion 102 is formed on the outer peripheral surface of the bearing portion 100. In accordance with an exemplary embodiment, the maximum radius d of the outer peripheral surface of the second non-cutting portion 102 can be equal to the maximum radius b of the outer peripheral surface of the second cutting portion 91, or can be smaller than the maximum radius b. The drive shaft 30 is fixed to the inner peripheral surface of the structure 90.

When the medical device 80 is used, if the drive shaft 30 is rotated, the structure 90 interlocked with the drive shaft 30 is rotated. The structure 90 is rotatably supported by the bearing portion 100 via the spherical body 97. When the structure 90 is rotated, the spherical bodies 97 accommodated in the hole portions 98 are rotated and moved in the circumferential direction along the groove portions 101 of the bearing portion 100. In this manner, the structure 90 can be rather smoothly rotated in the distal portion of the outer tube 110. In addition, the aspiration force is applied to a gap between the outer tube 110 and the drive shaft 30. In this manner, the cut debris can be aspirated via the cutout portions 92 and the slits 95.

In addition, the outer peripheral surface of at least one of the first cutting portion 21 and the second cutting portion 91 (second cutting portion 91 in the example illustrated FIGS. 8 to 10) has a concave portion in the axially orthogonal cross section. That is, the second cutting portion 91 has the cutout portions 92. Since the structure 90 has the cutout portions 92, the structure 90 does not come into continuous contact with the vascular wall. Therefore, damage caused by frictional heat between the structure 90 and the vascular wall can be reduced.

Figure 11:
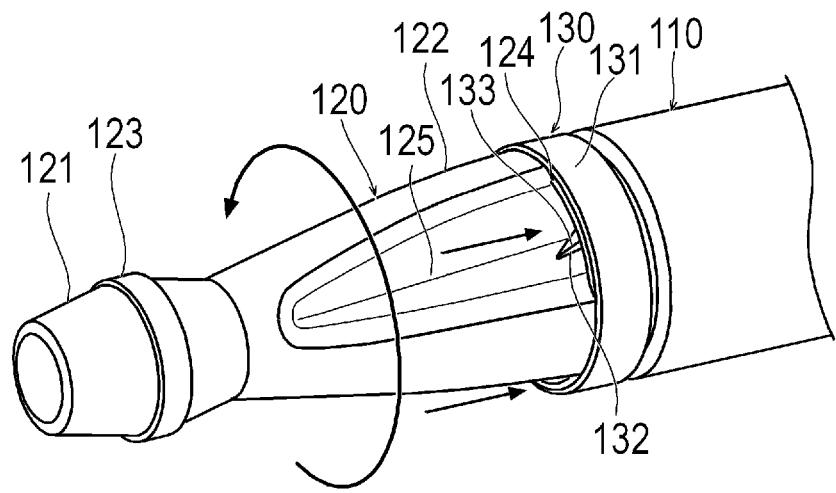
FIG. 11 is a perspective view illustrating still another modification example of the medical device.
Figure 12:
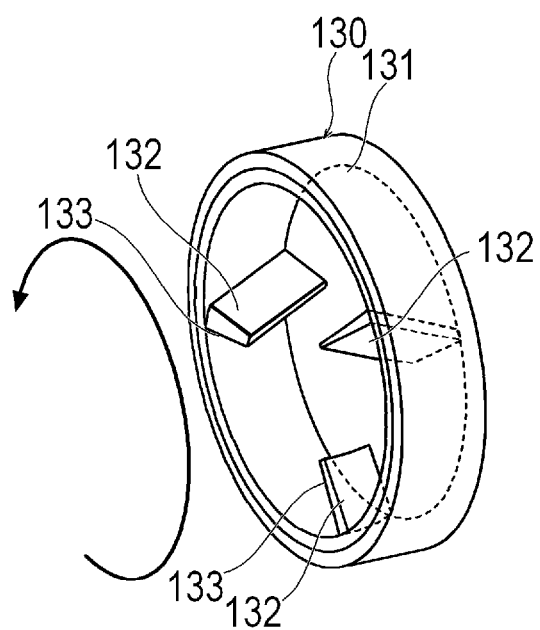
FIG. 12 is a perspective view illustrating an annular portion.

In addition, as in still another modification example illustrated in FIGS. 11 and 12, the second non-cutting portion 131 may be disposed in a member which is joined to a structure 120 and which is different from the structure 120. The same reference numerals will be given to elements having the same functions as those according to the above-described embodiment, and description of the reference numbers and functions will be omitted.

In accordance with an exemplary embodiment, the second non-cutting portion 131 is disposed in an annular portion 130 surrounding a step portion 124 formed on the outer peripheral surface of the proximal portion of the structure 120. The structure 120 has a first cutting portion 121, a second cutting portion 122, a first non-cutting portion 123, and the step portion 124. The step portion 124 is a portion to which the annular portion 130 is fixed. The step portion 124 is formed on the outer peripheral surface of the proximal portion of the structure 120. The step portion 124 can be continuously formed from the second cutting portion 122 to the proximal side, and has the smaller outer diameter than the second cutting portion 122. The outer peripheral surfaces of the second cutting portion 122 and the step portion 124 have a cutout portion 125 cut into a substantially V-shape in the axially orthogonal cross section. In accordance with an exemplary embodiment, abrasive grains (not illustrated) can be disposed on the outer peripheral surfaces of the first cutting portion 121 and the second cutting portion 122. The maximum outer diameter b of the second cutting portion 122 where the abrasive grains are disposed can be equal to the maximum outer diameter d of the second non-cutting portion 131, or can be larger than the maximum outer diameter d.

In accordance with an exemplary embodiment, the annular portion 130 is fitted and fixed to the step portion 124. The annular portion 130 can be, for example, preferably fixed to the step portion 124 by means of welding. The outer peripheral surface of the annular portion 130 has the second non-cutting portion 131. Blades 132 extending toward the center are formed on the inner peripheral surface of the annular portion 130. The vane 132 is located in a flow path formed between the inner peripheral surface of the annular portion 130 and the cutout portion 125. The vane 132 can be inclined so that the distal end and the proximal end are shifted in the circumferential direction. Therefore, the vane 132 is rotated, thereby enabling a fluid or an object inside the flow path to move to the proximal side. In this manner, the vane 132 can be rotated together with the structure 120, thereby generating a flow toward the proximal side, and thus, the cut debris can be aspirated. In addition, a sharp blade 133 may be formed in the edge portion on the distal side of the vane 132. The blade 133 can cut the aspirated debris into smaller pieces. Therefore, the medical device can cut, aspirate, and remove the large debris. In accordance with an exemplary embodiment, the vane 132 may not be included in the flow path inner peripheral surface of the annular portion 132 and the cutout portion 125.

Figure 13:
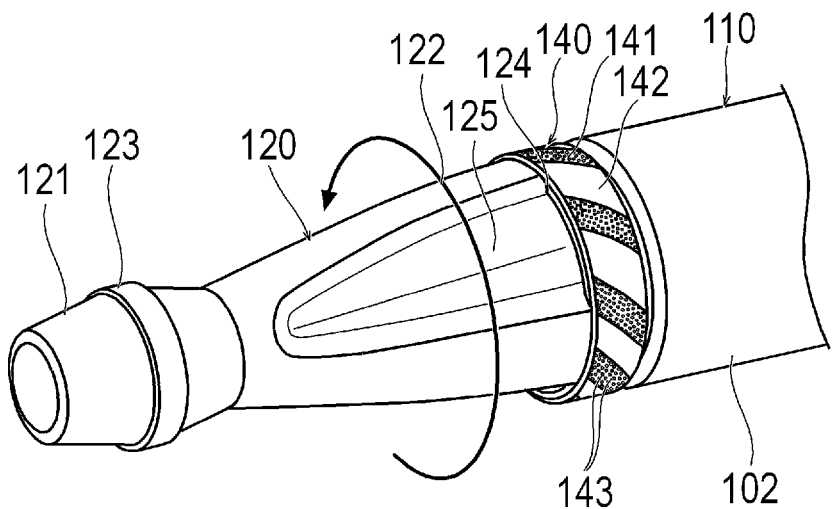
FIG. 13 is a perspective view illustrating still another modification example of the medical device.

In addition, as in still another modification example illustrated in FIG. 13, an annular portion 140 joined to the structure 120 may have abrasive grains 143 disposed in a portion of the outer peripheral surface. The same reference numerals will be given to elements having the same functions as those according to the above-described embodiment, and description of the reference numbers and functions will be omitted. In accordance with an exemplary embodiment, the outer peripheral surface of the annular portion 140 and the second cutting portion 122 of the structure 120 form the cutting portion (second cutting portion). The second non-cutting portion 102 is disposed on the outer peripheral surface of the bearing portion 100 located on the proximal side of the annular portion 140.

In accordance with an exemplary embodiment, the outer peripheral surface of the annular portion 140 has a cutting surface 141 inclined in a spiral shape with respect to the axis center, and a non-cutting surface 142. The cutting surface 141 and the non-cutting surface 142 can be alternately arranged in parallel in the circumferential direction. A plurality of the abrasive grains 143 are fixed to the surface of the cutting surface 141.

If the structure 120 and the annular portion 140 are rotated, since the cutting surface 141 is inclined with respect to the axis center, the cutting surface 141 receives force acting in the axial direction from a contact target. In this manner, the annular portion 140 receives the force acting toward the distal side (or the proximal side) inside the stenosed site S. Therefore, the medical device can be rather easily moved along the axial direction inside the stenosed site S. As the stenosed site S is narrowed, the annular portion 140 receives the stronger force from the contact target, and the medical device can be rather easily moved along the axial direction.

In addition, the first non-cutting portion 23 and the second non-cutting portion 24 may have a cutting capability to a certain extent, as long as the cutting capability is lower than that of the first cutting portion 21 and the second cutting portion 22. The cutting capacity can be compared depending on a cutting volume (cuttable volume of a cutting target) within the same time under the same cutting condition (force of pressing the cutting portion against the cutting target and speed of moving the cutting portion with respect to the cutting target). For example, at least one surface of the first non-cutting portion 23 and the second non-cutting portion 24 has abrasive grains (irregularities) smaller than the abrasive grains 72 of the first cutting portion 21 and the second cutting portion 22. In accordance with an exemplary embodiment, a size (height) of the abrasive grains disposed in the first non-cutting portion 23 and the second non-cutting portion 24 can be, for example, preferably 30 µm or smaller. Alternatively, at least one of the first non-cutting portion 23 and the second non-cutting portion 24 may have the abrasive grains. The number of the abrasive grains per unit area of the first non-cutting portion 23 and the second non-cutting portion 24 may be smaller than the number of abrasive grains per unit area of the first cutting portion 21 and the second cutting portion 22. In this case, the size of the abrasive grains disposed in the first non-cutting portion 23 and the second non-cutting portion 24 may be approximately the same as the size of the abrasive grains 72 disposed in the first cutting portion 21 and the second cutting portion 22. In addition, at least one of the first non-cutting portion 23 and the second non-cutting portion 24 may have the abrasive grains. In accordance with an exemplary embodiment, where the number of the abrasive grains per unit area of the first non-cutting portion 23 and the second non-cutting portion 24 is the same as the number of the abrasive grains per unit area of the first cutting portion 21 and the second cutting portion 22, the size of the abrasive grains of at least one of the first non-cutting portion 23 and the second non-cutting portion 24 may be smaller than the size of the abrasive grains of the first cutting portion 21 and the second cutting portion 22. In addition, the outer surface of the first cutting portion 21 and the second cutting portion 22 may have a blade or a groove instead of the abrasive grains. In this case, at least one outer surface of the first non-cutting portion 23 and the second non-cutting portion 24 may not have the blade or the groove. Alternatively, at least one outer surface of the first non-cutting portion 23 and the second non-cutting portion 24 may have another blade or another groove smaller than the blade or the groove of the first cutting portion 21 and the second cutting portion 22. In addition, at least one of the first non-cutting portion 23 and the second non-cutting portion 24 may have the blade or the groove. The number of the blades or the grooves per unit area of the first non-cutting portion 23 and the second non-cutting portion 24 may be smaller than the number of the blades or the grooves per unit area of the first cutting portion 21 and the second cutting portion 22. As illustrated in FIG. 4C described above, if the first non-cutting portion 23 passes through the stenosed site S on the distal side, the first non-cutting portion 23 does not receive the force from the stenosed site S. Accordingly, the force of pressing the first cutting portion 21 against the vascular wall can be significantly weakened. Therefore, even if the first non-cutting portion 23 has the cutting capacity to some degree, the damage to the vascular wall which is caused by the first non-cutting portion 23 can be limited. Therefore, the first non-cutting portion 23 may have the cutting capacity to some degree.

Figure 14:
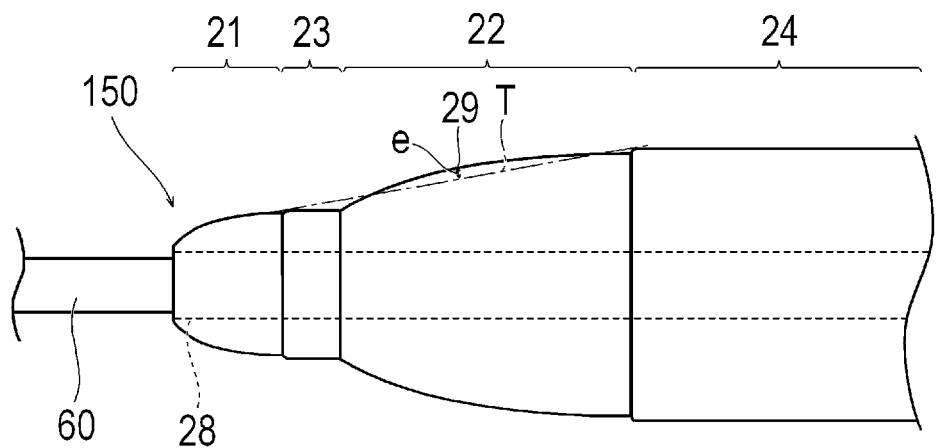
FIG. 14 is a plan view illustrating still another modification example of the medical device.

In addition, as in still another modification example illustrated in FIG. 14, a portion having the maximum outer diameter of the structure 150 may be the second non-cutting portion 24. The outer diameter of the first cutting portion 21 and the second cutting portion 22 gradually increases from the distal side toward the proximal side. In accordance with an exemplary embodiment, the maximum outer diameter of the second cutting portion 22 can be larger than the maximum outer diameter of the first cutting portion 21, and can be larger than the maximum outer diameter of the first non-cutting portion 23. The outer diameter of the second cutting portion 22 can be formed in a convex shape protruding outward in the radial direction in the cross section along the axial direction. The outer diameter of the first cutting portion 21 may be formed in a convex shape protruding outward in the radial direction in the cross section along the axial direction, but may not be formed in the convex shape. In accordance with an exemplary embodiment, a portion having the maximum outer diameter of the first cutting portion 21 can be located on the proximal side of the first cutting portion 21. A portion having the maximum outer diameter of the second cutting portion 22 can be located on the proximal side of the second cutting portion 22. A portion of the second cutting portion 22 deviates outward in the radial direction from the tangent T to the first non-cutting portion 23 and the second non-cutting portion 24 in the cross section along the axial direction. In the cross section along the axial direction of the structure 150, the deviation distance e from the tangent T to the most distant portion 29 most distant in a direction perpendicular to the tangent T and away from the central axis of the structure 150 is preferably, for example, smaller than the thickness of the vascular wall.

As described above, the second cutting portion 22 gradually increases from the distal side to the proximal side, and a portion having the maximum outer diameter of the second cutting portion 22 is located on the proximal side of the second cutting portion 22. At least a portion of the second cutting portion 22 is located outside the tangent to the first non-cutting portion 23 and the second non-cutting portion 24 in the cross section along the axial direction of the structure 150. In this manner, in the medical device, the second cutting portion 22 whose outer diameter gradually increases to the proximal side can be moved rather easily to the distal side, and the medical device can cut the stenosed site S inside the biological lumen rather effectively. Then, a portion having the maximum outer diameter of the second cutting portion 22 is disposed close to the second non-cutting portion 24. Accordingly, the movement in the radial direction of the structure 150 can be regulated. Therefore, in the medical device, the second non-cutting portion 24 can help prevent the vascular wall from being excessively damaged by the second cutting portion 22 such as vascular wall perforation. Therefore, the medical device can compatibly achieve improved cutting capacity and improved safety. In accordance with an exemplary embodiment, the maximum outer diameter means the maximum outer diameter of a locus obtained when the medical device is rotated. Therefore, each cross-sectional shape of the first cutting portion 21, the second cutting portion 22, the first non-cutting portion 23, and the second non-cutting portion 24 may not be a circular shape. A difference between the maximum outer diameter of the second cutting portion 22 and the maximum outer diameter of the second non-cutting portion 24 can be smaller than the maximum value of the thickness of the biological lumen such as the blood vessel. Furthermore, the difference can be, for example, preferably smaller than the minimum value of the thickness of the biological lumen. As described above, the maximum value of the thickness of the blood vessel can be, for example, 150 µm, and the minimum value of the thickness of the blood vessel can be, for example, 20 µm.

In addition, in the cross-section along the axial direction of the structure 150, the deviation distance e from the tangent T to the most distant portion 29 most distant in the direction perpendicular to the tangent T and away from the central axis of the structure 150 can be smaller than the maximum value (for example, 150 µm) of the thickness of the vascular wall. In this manner, the vascular wall can be prevented from being excessively cut by the second cutting portion 22, thereby improving the safety. The deviation distance e may be smaller than the minimum value (for example, 20 µm) of the thickness of the vascular wall. In this case, the vascular wall can be further prevented from being excessively cut by the second cutting portion 22, thereby further improving the safety.

In addition, the most distant portion 29 may be located more proximal than the axial center of the second cutting portion 22. In this manner, the most distant portion 29 having the improved cutting capacity is located on the proximal side between the first non-cutting portion 23 and the second non-cutting portion 24. Therefore, compared to a case where the most distant portion 29 is located on the distal side of the second cutting portion 22, the most distant portion 29 comes into contact with the stenosed site S later when the second cutting portion 22 is pushed into the distal side. Therefore, the medical device can gradually and largely cut the stenosed site S. Accordingly, the medical device can safely and smoothly cut the stenosed site S.

In addition, the most distant portion 29 may be located more distal than the axial center of the second cutting portion 22. In this manner, the most distant portion 29 having the improved cutting capacity is located on the distal side between the first non-cutting portion 23 and the second non-cutting portion 24. Therefore, compared to a case where the most distant portion 29 is located on the proximal side of the second cutting portion 22, the most distant portion 29 comes into contact with the stenosed site S earlier when the second cutting portion 22 is pushed into the distal side. Therefore, the medical device can achieve the improved cutting capacity while the safety can be relatively ensured by the first non-cutting portion 23 and the second non-cutting portion 24.

In addition, the maximum outer diameter of the second non-cutting portion 24 can be larger than the maximum outer diameter of the first cutting portion 21, the second cutting portion 22, and the first non-cutting portion 23. That is, a portion having the maximum outer diameter of the structure 150 can be the second non-cutting portion 24. Therefore, the vascular wall can be prevented from being excessively cut by the first cutting portion 21 and the second cutting portion 22, thereby improving the relative safety. In accordance with an exemplary embodiment, the second non-cutting portion 24 may not be a portion of the structure 150. The second non-cutting portion 24 may be a tubular body located on the proximal side of the structure 150. Therefore, the second non-cutting portion 24 may not be rotated together with the structure 150.

In accordance with an exemplary embodiment, a portion having the maximum outer diameter of the structure may be the second cutting portion. In this case, the stenosed site S can be effectively cut by the second cutting portion.

In addition, the outer diameter of the first non-cutting portion 23 can be smaller than the outer diameter of the second non-cutting portion 24. Therefore, when the structure 150 is pushed into the distal side, the second cutting portion 22 located between the first non-cutting portion 23 and the second non-cutting portion 24 can be effectively brought into contact with the stenosed site S. In addition, in a case where the axial length of the second cutting portion 22 is equal and the axial length of the second cutting portion 22 deviating outward in the radial direction from the tangent T to the first non-cutting portion 23 and the second non-cutting portion 24 in the cross section along the axial direction is also equal, if the outer diameter of the first non-cutting portion 23 is smaller than the outer diameter of the second non-cutting portion 24, a surface area of the deviating second cutting portion 22 can be larger than that in a case where the outer diameter of the first non-cutting portion 23 is substantially the same as the outer diameter of the second non-cutting portion 24. Therefore, in a case where the outer diameter of the first non-cutting portion 23 is smaller than the outer diameter of the second non-cutting portion 24, the object can be cut rather easily within a shorter time, compared to a case where the outer diameter of the first non-cutting portion 23 is substantially the same as the outer diameter of the second non-cutting portion 24.

In addition, as the total axial length from the first cutting portion 21 to the distal end of the second cutting portion 22 or the second non-cutting portion 24 decreases, the ability of the medical device to follow the guide wire becomes improved. Therefore, it can be preferable that the total length from the first cutting portion 21 to the distal end of the second cutting portion 22 or the second non-cutting portion 24 is relatively short. In order to set the surface area size of the protruding portion from the tangent T of the second cutting portion 22 to be substantially equal, compared to a case where the outer diameter of the first non-cutting portion 23 is approximately the same as the outer diameter of the second non-cutting portion 24, the axial length of the second cutting portion 22 can be shortened in a case where the outer diameter of the first non-cutting portion 23 is smaller than the outer diameter of the second non-cutting portion 24. Therefore, since the outer diameter of the first non-cutting portion 23 is smaller than the outer diameter of the second non-cutting portion 24, the ability of the medical device to follow the guide wire can be improved.

The detailed description above describes to a medical device and treatment device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object inside a biological lumen, the medical comprising:
   a rotatable drive shaft;
   a structure configured to be connected with a distal portion of the drive shaft and rotatable by the drive shaft;
   the structure having a cutting portion having an outer peripheral surface configured to cut the object, and a non-cutting portion having an outer peripheral surface, the cutting portion having a first cutting portion and a second cutting portion located proximal to the first cutting portion;
   the non-cutting portion includes a first non-cutting portion and a second non-cutting portion, the first non-cutting portion located between the first cutting portion and the second cutting portion, and the second non-cutting portion located on a proximal side of the second cutting portion;

a tubular body disposed on the proximal side of the second cutting portion of the structure; and wherein the medical device satisfies Equations (A) to (E):

$$a<b \quad \text{Equation (A)}$$

$$c<d \quad \text{Equation (B)}$$

$$d \leq b \quad \text{Equation (C)}$$

$$a<d \quad \text{Equation (D)}$$

$$L1<L2 \quad \text{Equation (E)}$$

wherein a represents a maximum radius of an outer peripheral surface of the first cutting portion, b represents a maximum radius of an outer peripheral surface of the second cutting portion, c represents a maximum radius of an outer peripheral surface of the first non-cutting portion, d represents a maximum radius of an outer peripheral surface of the second non-cutting portion, L1 represents an axial length of the first non-cutting portion, and L2 represents an axial length of the second cutting portion.

2. The medical device according to claim 1, wherein the medical device further satisfies Equation (F):

$$a-100 \text{ μm} \leq c<b \quad \text{Equation (F)}.$$

3. The medical device according to claim 1, wherein the medical device satisfies Equation (G):

$$a-ai+e<b \quad \text{Equation (G)}$$

wherein ai represents a minimum radius of a range in which the first cutting portion can perform cutting, and e represents a deviation distance from a tangent to the first non-cutting portion and the second non-cutting portion to a most distant portion of the second cutting portion, which is most distant in a direction perpendicular to the tangent and away from a central axis of the structure, in a cross section along an axial direction of the structure.

4. The medical device according to claim 1, wherein the second cutting portion has a diameter decreasing portion whose outer diameter decreases in a tapered shape toward a distal side.

5. The medical device according to claim 1, wherein the second cutting portion has a diameter increasing portion whose outer diameter increases in a tapered shape toward a distal side.

6. The medical device according to claim 1, wherein at least a portion of the first cutting portion has an outer diameter decreasing in a tapered shape toward a distal side.

7. The medical device according to claim 1, wherein an outer peripheral surface of at least one of the first cutting portion and the second cutting portion has a concave portion in an axially orthogonal cross section.

8. A medical device for cutting an object inside a biological lumen, comprising:

a rotatable drive shaft;

a structure configured to be connected with a distal portion of the drive shaft and rotatable by the drive shaft;

the structure having a cutting portion having an outer peripheral surface configured to cut the object, and a non-cutting portion having an outer peripheral surface;

the non-cutting portion includes a first non-cutting portion and a second non-cutting portion, the first non-cutting portion located on a distal side of the cutting portion, and the second non-cutting portion located on a proximal side of the cutting portion;

a tubular body disposed on a proximal side of the cutting portion of the structure; and wherein the medical device is configured to satisfy Equations (B) and (H):

$$c<d \quad \text{Equation (B)}$$

$$e<150 \text{ μm} \quad \text{Equation (H)}$$

wherein c represents a maximum radius of an outer peripheral surface of the first non-cutting portion, d represents a maximum radius of an outer peripheral surface of the second non-cutting portion, and e represents a deviation distance from a tangent to the first non-cutting portion and the second non-cutting portion to a most distant portion of the cutting portion, which is most distant in a direction perpendicular to the tangent and away from a central axis of the structure, in a cross section along an axial direction of the structure.

9. The medical device according to claim 8, wherein the cutting portion has a first cutting portion and a second cutting portion located more proximal than the first cutting portion;

the first cutting portion is located on a distal side of the first non-cutting portion;

the second cutting portion is located on a distal side of the second non-cutting portion and on a proximal side of the first non-cutting portion; and the most distant portion is located in the second cutting portion.

10. The medical device according to claim 8, wherein the cutting portion has a second cutting portion located on a distal side of the second non-cutting portion and on a proximal side of the first non-cutting portion;

the second cutting portion has a distal cutting portion including a portion whose outer diameter increases toward a distal side, and a proximal cutting portion located on a distal side of the second non-cutting portion and on a proximal side of the distal cutting portion, and including a portion whose outer diameter decreases toward a distal side;

the distal cutting portion is located closer to a central axis of the structure than the tangent in a direction perpendicular to the tangent and toward the central axis; and the most distant portion is located in the proximal cutting portion.

11. A medical device for cutting an object inside a biological lumen, comprising:

a rotatable drive shaft; and a structure configured to be connected to a distal portion of the drive shaft and rotatable by the drive shaft, wherein the structure has a cutting portion having an outer peripheral surface capable of cutting the object, and a non-cutting portion having an outer peripheral surface;

the cutting portion includes a first cutting portion and a second cutting portion located more proximal than the first cutting portion;

the non-cutting portion being located on a proximal portion of the second cutting portion of the structure;

a tubular body disposed on a proximal side of the second cutting portion of the structure;

the second cutting portion gradually increases in diameter from a distal side to a proximal side, and a maximum outer diameter of the second cutting portion is located on a proximal portion of the second cutting portion; and at least a portion of the second cutting portion is located outside a tangent to the non-cutting portion in a cross section along an axial direction of the structure.

12. The medical device according to claim 11, wherein the non-cutting portion includes a first non-cutting portion and a second non-cutting portion, the first non-cutting portion located between the first cutting portion and the second cutting portion, and the second non-cutting portion located on a proximal side of the second cutting portion; and a deviation distance from the tangent to the first non-cutting portion and the second non-cutting portion to a most distant portion of the second cutting portion, which is most distant in a direction perpendicular to the tangent and away from a central axis of the structure, in the cross section along the axial direction of the structure is smaller than 150 µm.

13. The medical device according to claim 12, wherein the most distant portion of the second cutting portion is located more proximal than an axial center of the second cutting portion.

14. The medical device according to claim 12, wherein the most distant portion of the second cutting portion is located more distal than an axial center of the second cutting portion.

15. The medical device according to claim 11, wherein the non-cutting portion includes a first non-cutting portion and a second non-cutting portion, the first non-cutting portion located between the first cutting portion and the second cutting portion, and the second non-cutting portion located on a proximal side of the second cutting portion; and a maximum outer diameter of the second non-cutting portion is larger than a maximum outer diameter of the first cutting portion, the maximum outer diameter of the second cutting portion, and a maximum outer diameter of the first non-cutting portion.

16. The medical device according to claim 11, wherein a portion of the structure having a maximum outer diameter is the second cutting portion.

17. The medical device according to claim 11, wherein the non-cutting portion includes a first non-cutting portion and a second non-cutting portion, the first non-cutting portion located between the first cutting portion and the second cutting portion, and the second non-cutting portion located on a proximal side of the second cutting portion; and an outer diameter of the first non-cutting portion is smaller than an outer diameter of the second non-cutting portion.

18. A treatment method for cutting an object inside a biological lumen by using the medical device according to claim 1, the method comprising:

inserting the structure into the biological lumen;

bringing the first non-cutting portion into smooth contact with a biological tissue by moving the structure to the distal side while rotating the structure, and causing the first cutting portion to cut the object; and bringing the first non-cutting portion and the second non-cutting portion into contact with the biological tissue by moving the structure to the distal side, and rotating the structure to cause the second cutting portion to cut the object.

19. The treatment method according to claim 18, further comprising:

removing the structure from the inside of the biological lumen.

20. The treatment method according to claim 18, further comprising:

causing a rotary shaft of the structure to oscillate by bending a bent portion of an outer sheath of the structure at a predetermined angle to change a direction of a distal portion of the outer sheath;

rotating the rotary shaft of the structure and imparting an oscillating motion to the structure; and cutting the object with the structure.

* * * * *